(12) United States Patent
Gordon et al.

(10) Patent No.: US 6,825,033 B2
(45) Date of Patent: Nov. 30, 2004

(54) MUTATED CYCLIN G1 PROTEIN

(75) Inventors: Erlinda Maria Gordon, Glendale, CA (US); Frederick L. Hall, Glendale, CA (US)

(73) Assignee: University of Southern California, Los Angeles, CA (US)

(*) Notice: Subject to any disclaimer, the term of this patent is extended or adjusted under 35 U.S.C. 154(b) by 104 days.

(21) Appl. No.: 09/796,149

(22) Filed: Feb. 28, 2001

(65) Prior Publication Data

US 2002/0035079 A1 Mar. 21, 2002

Related U.S. Application Data

(60) Provisional application No. 60/325,765, filed on Mar. 2, 2000, now abandoned.

(51) Int. Cl.[7] .................. C12N 15/85; C12N 15/861; C12N 15/867; C07H 21/04

(52) U.S. Cl. .................. 435/320.1; 536/23.5

(58) Field of Search .................. 536/23.5; 435/320.1

(56) References Cited

FOREIGN PATENT DOCUMENTS

| WO | WO 94/26888 | 11/1994 |
|---|---|---|
| WO | WO 97/16209 | 5/1997 |
| WO | WO 98/18826 | 5/1998 |

OTHER PUBLICATIONS

Draetta, G., "Mammalian $G_1$ Cyclins," *Curr. Opin. Cell Biol.*, 6:842–846 (1994).
Gordon, et al., "Inhibition of Metastatic Tumor Growth in Nude Mice by Portal Vein Infusions of Matrix–targeted Retroviral Vectors Bearing a Cytocidal Cyclin G1 Construct," *Cancer Research*. 60:3343–3347 (Jul. 1, 2000).
Gordon, et al., "Systemic Administration of a Matrix–Targeted Retroviral Vector is Efficacious for Cancer Gene Therapy in Mice," *Human Gene Therapy*, 12:193–204 (Jan. 20, (2001).
Grunhaus, et al., "Adenoviruses as Cloning Vectors," *Virology*, 3:237–252 (1992).
Horne, et al., "Cyclin G1 and Cyclin G2 Comprise a New Family of Cyclins with Contrasting Tissue–specific and Cell Cycle–regulated Expression," *J. Biol. Chem.*, 271(11):6050–6061 (Mar. 15, 1996).
International Search Report for PCT Application No. PCT/IB01/00303.
Kampmeier, et al., "Inhibition of Rabbit Keratocyte and Human Fetal Lens Epithelial Cell Proliferation by Retrovirus–Mediated Transfer of Antisense Cyclin G1 and Antisense MAT1 Constructs," *Human Gene Therapy*, 11:1–8 (Jan. 1, 2000).
Majors, J.E., "Retroviral Vectors—Strategies and Applications," *Virology*, 3:285–295 (1992).
McKnight, et al., "Inhibition of Human Immunodeficiency Virus Fusion by a Monoclonal Antibody to a Coreceptor (CXCR4) is Both Cell Type and Virus Strain Dependent," *Journal of Virology*, 71(2):1692–1696 (Feb. 1997).

(List continued on next page.)

*Primary Examiner*—Terry McKelvey
*Assistant Examiner*—Nancy T. Vogel
(74) *Attorney, Agent, or Firm*—Elliot M. Olstein; Raymond J. Lillie

(57) ABSTRACT

Methods of treating tumors, preventing restenosis, and treating hyperplasias, corneal haze, and cataracts by administering to an animal a mutated cyclin G1 protein. The mutated cyclin G1 protein may be administered to an animal by administering to an animal an expression vehicle, such as a retroviral vector comprising a gene construct encoding a mutated cyclin G1 protein.

10 Claims, 16 Drawing Sheets-

OTHER PUBLICATIONS

Steinberger, et al., "Functional Deletion of the CCR5 Receptor by Intracellular Immunization Produces Cells that are Refractory to CCR5–Dependent HIV–1 Infection and Cell Fusion," *Proceedings of the National Academy of Sciences of the United States of America*, 97(2):805–810 (Jan. 18, 2000).

Steinberger, et al., "Generation and Characterization of a Recombinant Human CCR5–Specific Antibody. A Phage Display Approach for Rabbit Antibody Humanization," *Journal of Biological Chemistry*, 275(46):36073–36078 (Nov. 17, 2000).

Skotzko, et al., "Retroviral Vector–mediated Gene Transfer of Antisense Cycle G1 (*CYCG1*) Inhibits Proliferation of Human Osteogenic Sarcoma Cells," *Cancer Research*, 55:5493–5498 (Dec. 1, 1995).

Tamura, et al., "Cyclin G: A New Mammalian Cyclin with Homology to Fission Yeast Cig1," *Oncogene*, 8:2113–2118 (1993).

Wu, et al., "Molecular Cloning of the Human *CYCG1* Gene Encoding a G–type Cyclin: Overexpression in Human Osteosarcoma Cells," *Oncology Reports*, 1:705–711 (1994).

Figure 1 A & B
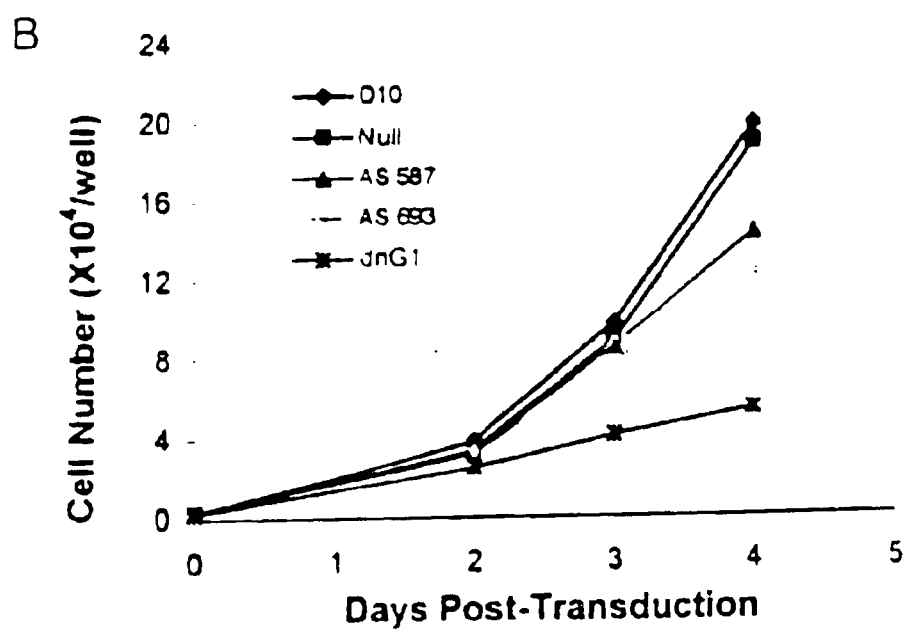

Figure 4

```
                          α1                          α2
Hum CycG1    1    MTARLRDFEVKDLLSLTQPFGFDTETFSLAVNLLDRFLSKMKVQPKHLGC    50
Hum Cyc1    40    VSPSQRDEVIQWLAKLKYQFNLYPETFALASSLLDRFLATVKAHPKYLSC    89
Hum CycA   206    QTNSMRAILVDWLVEVGEEYKLQNETLHLAVNYIDRFLSSMSVLRGKLQL   255
S.Pom Cig1 191    QDWVTRHMLVDWITQVQIHFRLLPETLFLAVNLIDRFLSIKVVSLQKVQL   240

α3      *               α4            α5       *
Hum CycG1   51    VGLSCFYLAVKSIDEERNVPLATDLIRTSQYRFDVSDLMRMEKIVLEKVC   100
Hum Cyc1    90    IAISCFFLAAKTVDEDERIPVLKVLARQSFCGCDSSEILRMERIILDKLN   139
Hum CycA   256    VGTAAMLLASKFEE--IYPPEVAEFVYITDDTYTKKQVLRMEHLVLKVLT   303
S.Pom Cig1 241    VGLSALLIACKYED--IHPPSIYNFAHWVQGIFTVDEIIRAERYMLMLUD   288

α1'                         α2'
Hum CycG1  101    WKWKATTAFQFLQLYYSLLQEMLP-----LDRRN-SINFERLEAQLKACH   144
Hum Cyc1   140    WDUHTATPLDFLHIFHAIAVSTRPQLLFSLRKLSPSQHLAVLTKQLLHCM   189
Hum CycA   304    FDQAAPTVNQFLTQYFLHQQPA--------NCK-VESLAMFLGELSLLD   343
S.Pom Cig1 289    FDDSWPGPMSFLRRISRAHSYD--------HD-IRMLAKYLQEVTLMD   327

α3'                        α4'
Hum CycG1  145    CRIIFSKAMPSVLALSIIALEIQAQKCVELTEGDECLQKHSMINGRDLTF   194
Hum Cyc1   190    ACNQLLQFRGSMLALAMVSLEMEKLIPDWLSLTDELLQK-AQMDSSQLIH   238
Hum CycA   344    ADPYL-KYUPSVIAGAAFHLALYTWTGQSWP---ESLIRKTG-------Y   382
S.Pom Cig1 328    -EIFI-GAKISFIAATAYYLSMQMUGHLDWT---PCHVYYSG-------Y   365

α5'
Hum CycG1  195    WQELVSKCLTEYSSNKCSKPNVQKLKWIVSGRTARQLKHSYYRITHLPTI   244
Hum Cyc1   239    QRELVAHHLSTLQSSLPLNSVYVYRPLKHTLVTCDKGVFRLHPSSVPGPD   288
Hum CycA   383    TLESLKPCLMDLHQTYLKAPQHAQ------QSIREKYKNSKYHGVSLLNP   426
S.Pom Cig1 366    TARQLKPCANIIWECDVDAPNH-H------NAIYRKYSENRMKRVSAFAH   408

Hum CycG1  245    PEMVP                                                249
Hum Cyc1   289    FSKON...                                             293
Hum CycA   427    PETLN...                                             431
S.Pom Cig1 409    NWVLS...                                             413
```

Figure 5
A
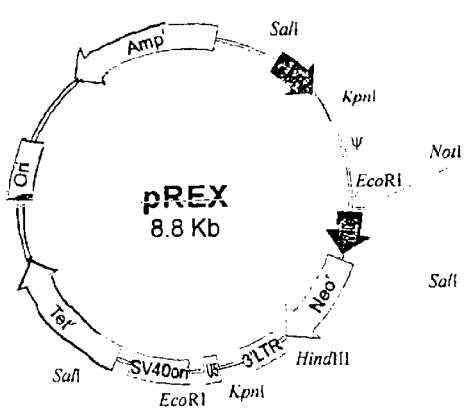
pREX Retroviral
Expression Vector
B Antisense Cyclin G1 Fragments:
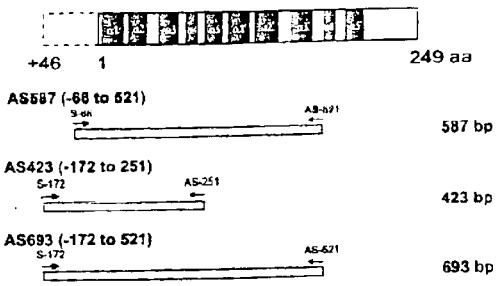
C Mutant Cyclin G1 Fragments:
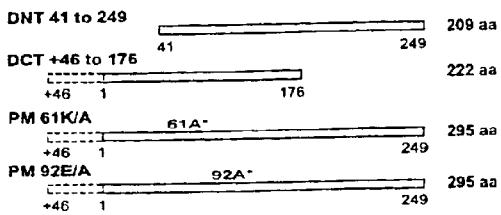

Figure 8
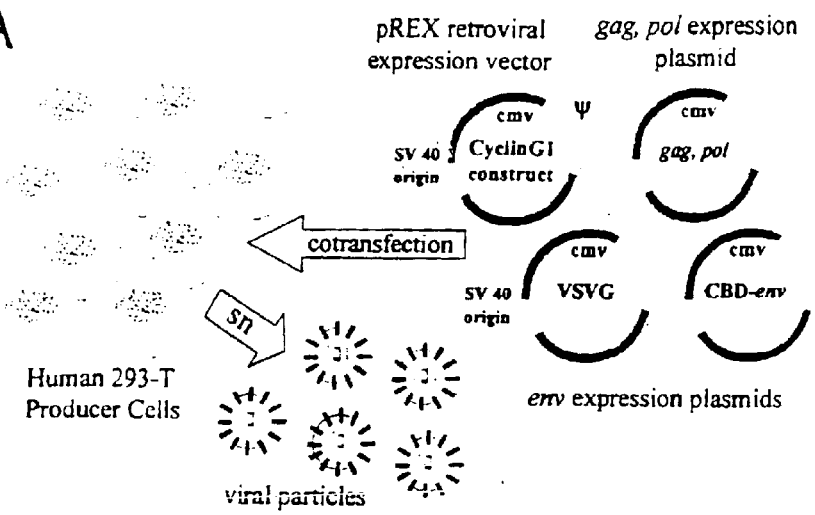
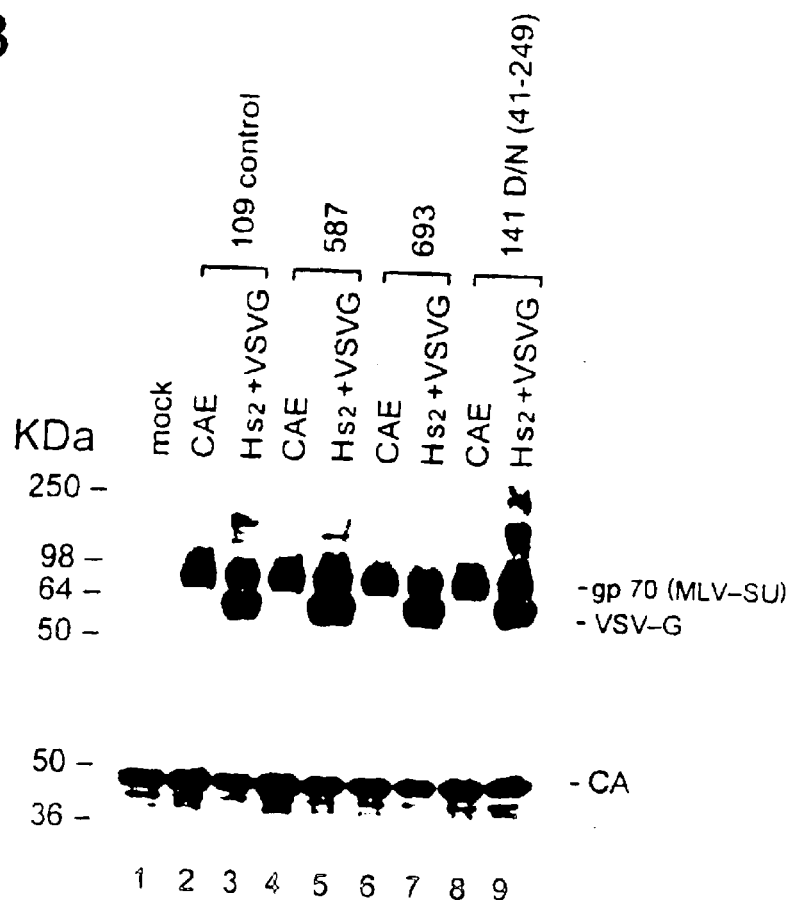

Figure 10
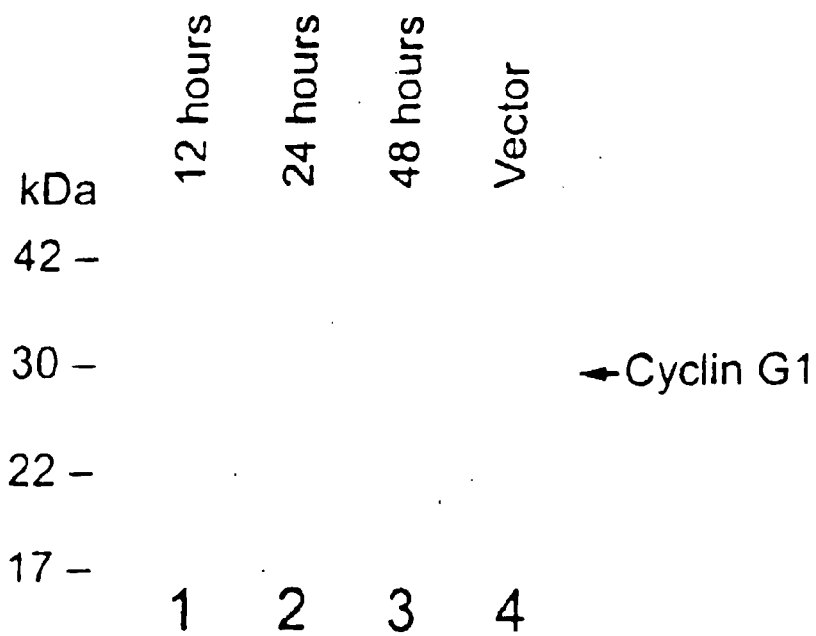
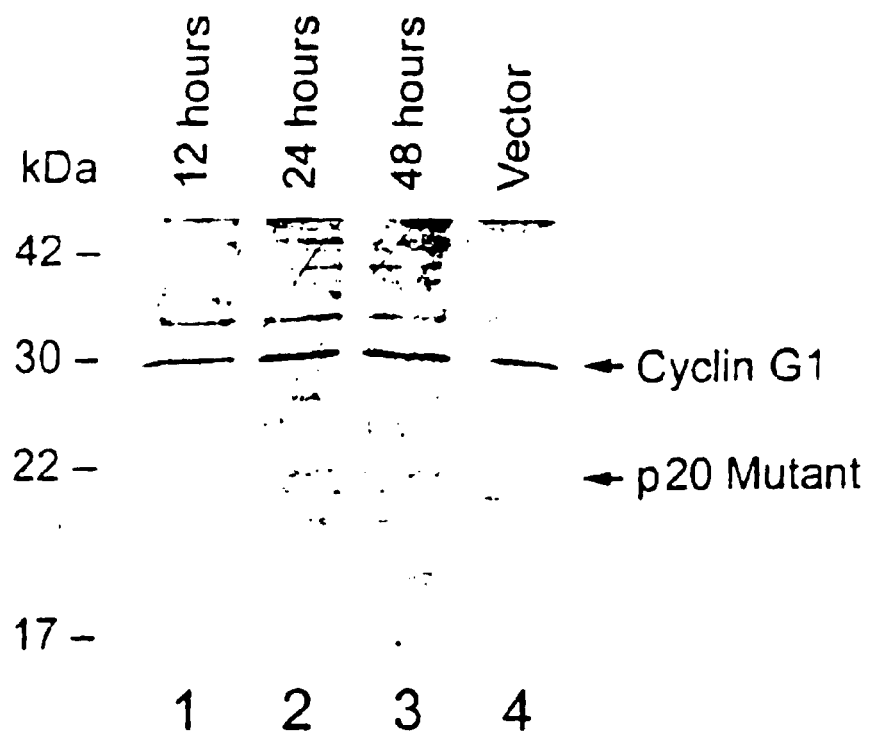

SEQUENCE LISTING

```
<160> NUMBER OF SEQ ID NOS: 8

<210> SEQ ID NO 1
<211> LENGTH: 10
<212> TYPE: PRT
<213> ORGANISM: Homo sapiens

<400> SEQUENCE: 1

Trp Arg Glu Pro Gly Arg Met Glu Leu Asn
1               5                   10

<210> SEQ ID NO 2
<211> LENGTH: 19
<212> TYPE: PRT
<213> ORGANISM: Homo sapiens

<400> SEQUENCE: 2

Cys Lys His Ser Tyr Tyr Arg Ile Thr His Leu Pro Thr Ile Pro Glu
1               5                   10                  15

Met Val Pro

<210> SEQ ID NO 3
<211> LENGTH: 249
<212> TYPE: PRT
<213> ORGANISM: Homo sapiens

<400> SEQUENCE: 3

Met Thr Ala Arg Leu Arg Asp Phe Glu Val Lys Asp Leu Leu Ser Leu
1               5                   10                  15

Thr Gln Phe Phe Gly Phe Asp Thr Glu Thr Phe Ser Leu Ala Val Asn
                20                  25                  30

Leu Leu Asp Arg Phe Leu Ser Lys Met Lys Val Gln Pro Lys His Leu
            35                  40                  45

Gly Cys Val Gly Leu Ser Cys Phe Tyr Leu Ala Val Lys Ser Ile Glu
    50                  55                  60

Glu Glu Arg Asn Val Pro Leu Ala Thr Asp Leu Ile Arg Ile Ser Gln
65                  70                  75                  80

Tyr Arg Phe Thr Val Ser Asp Leu Met Arg Met Glu Lys Ile Val Leu
                85                  90                  95

Glu Lys Val Cys Trp Lys Val Lys Ala Thr Thr Ala Phe Gln Phe Leu
            100                 105                 110

Gln Leu Tyr Tyr Ser Leu Leu Gln Glu Asn Leu Pro Leu Glu Arg Arg
        115                 120                 125

Asn Ser Ile Asn Phe Glu Arg Leu Glu Ala Gln Leu Lys Ala Cys His
    130                 135                 140

Cys Arg Ile Ile Phe Ser Lys Ala Lys Pro Ser Val Leu Ala Leu Ser
145                 150                 155                 160

Ile Ile Ala Leu Glu Ile Gln Ala Gln Lys Cys Val Glu Leu Thr Glu
                165                 170                 175

Gly Ile Glu Cys Leu Gln Lys His Ser Lys Ile Asn Gly Arg Asp Leu
            180                 185                 190
```

```
Thr Phe Trp Gln Glu Leu Val Ser Lys Cys Leu Thr Glu Tyr Ser Ser
            195                 200                 205

Asn Lys Cys Ser Lys Pro Asn Val Gln Lys Leu Lys Trp Ile Val Ser
            210                 215                 220

Gly Arg Thr Ala Arg Gln Leu Lys His Ser Tyr Tyr Arg Ile Thr His
225                 230                 235                 240

Leu Pro Thr Ile Pro Glu Met Val Pro
                245

<210> SEQ ID NO 4
<211> LENGTH: 254
<212> TYPE: PRT
<213> ORGANISM: Homo sapiens

<400> SEQUENCE: 4

Val Ser Pro Ser Gln Arg Asp Glu Val Ile Gln Trp Leu Ala Lys Leu
1               5                   10                  15

Lys Tyr Gln Phe Asn Leu Tyr Pro Glu Thr Phe Ala Leu Ala Ser Ser
            20                  25                  30

Leu Leu Asp Arg Phe Leu Ala Thr Val Lys Ala His Pro Lys Tyr Leu
            35                  40                  45

Ser Cys Ile Ala Ile Ser Cys Phe Leu Ala Ala Lys Thr Val Glu
    50                  55                  60

Glu Asp Glu Arg Ile Pro Val Leu Lys Val Leu Ala Arg Asp Ser Phe
65                  70                  75                  80

Cys Gly Cys Ser Ser Glu Ile Leu Arg Met Glu Arg Ile Ile Leu
                85                  90                  95

Asp Lys Leu Asn Trp Asp Leu His Thr Ala Thr Pro Leu Asp Phe Leu
            100                 105                 110

His Ile Phe His Ala Ile Ala Val Ser Thr Arg Pro Gln Leu Leu Phe
            115                 120                 125

Ser Leu Pro Lys Leu Ser Pro Ser Gln His Leu Ala Val Leu Thr Lys
    130                 135                 140

Gln Leu Leu His Cys Met Ala Cys Asn Gln Leu Leu Gln Phe Arg Gly
145                 150                 155                 160

Ser Met Leu Ala Leu Ala Met Val Ser Leu Glu Met Glu Lys Leu Ile
                165                 170                 175

Pro Asp Trp Leu Ser Leu Thr Ile Glu Leu Leu Gln Lys Ala Gln Met
            180                 185                 190

Asp Ser Ser Gln Leu Ile His Cys Arg Glu Leu Val Ala His His Leu
            195                 200                 205

Ser Thr Leu Gln Ser Ser Leu Pro Leu Asn Ser Val Tyr Val Tyr Arg
    210                 215                 220

Pro Leu Lys His Thr Leu Val Thr Cys Asp Lys Gly Val Phe Arg Leu
225                 230                 235                 240

His Pro Ser Ser Val Pro Gly Pro Asp Phe Ser Lys Asp Asn
                245                 250

<210> SEQ ID NO 5
<211> LENGTH: 226
<212> TYPE: PRT
<213> ORGANISM: Homo sapiens

<400> SEQUENCE: 5

Ile Thr Asn Ser Met Arg Ala Ile Leu Val Asp Trp Leu Val Glu Val
1               5                   10                  15
```

```
Gly Glu Glu Tyr Lys Leu Gln Asn Glu Thr Leu His Leu Ala Val Asn
                20                  25                  30

Tyr Ile Asp Arg Phe Leu Ser Ser Met Ser Val Leu Arg Gly Lys Leu
         35                  40                  45

Gln Leu Val Gly Thr Ala Ala Met Leu Leu Ala Ser Lys Phe Glu Glu
 50                  55                  60

Ile Tyr Pro Pro Glu Val Ala Glu Phe Val Tyr Ile Thr Asp Asp Thr
65                  70                  75                  80

Tyr Thr Lys Lys Gln Val Leu Arg Met Glu His Leu Val Leu Lys Val
                85                  90                  95

Leu Thr Phe Asp Leu Ala Ala Pro Thr Val Asn Gln Phe Leu Thr Gln
            100                 105                 110

Tyr Phe Leu His Gln Gln Pro Ala Asn Cys Lys Val Glu Ser Leu Ala
        115                 120                 125

Met Phe Leu Gly Glu Leu Ser Leu Ile Asp Ala Asp Pro Tyr Leu Lys
130                 135                 140

Tyr Leu Pro Ser Val Ile Ala Gly Ala Ala Phe His Leu Ala Leu Tyr
145                 150                 155                 160

Thr Val Thr Gly Gln Ser Trp Pro Glu Ser Leu Ile Arg Lys Thr Gly
                165                 170                 175

Tyr Thr Leu Glu Ser Leu Lys Pro Cys Leu Met Asp Leu His Gln Thr
            180                 185                 190

Tyr Leu Lys Ala Pro Gln His Ala Gln Gln Ser Ile Arg Glu Lys Tyr
        195                 200                 205

Lys Asn Ser Lys Tyr His Gly Val Ser Leu Leu Asn Pro Pro Glu Thr
210                 215                 220

Leu Asn
225

<210> SEQ ID NO 6
<211> LENGTH: 223
<212> TYPE: PRT
<213> ORGANISM: Schizosaccharomyces pombe

<400> SEQUENCE: 6

Ile Asp Trp Val Thr Arg His Met Leu Val Asp Trp Ile Val Gln Val
1               5                   10                  15

Gln Ile His Phe Arg Leu Leu Pro Glu Thr Leu Phe Leu Ala Val Asn
                20                  25                  30

Leu Ile Asp Arg Phe Leu Ser Ile Lys Val Val Ser Leu Gln Lys Val
         35                  40                  45

Gln Leu Val Gly Leu Ser Ala Leu Leu Ile Ala Cys Lys Tyr Glu Glu
 50                  55                  60

Ile His Pro Pro Ser Ile Tyr Asn Phe Ala His Val Val Gln Gly Ile
65                  70                  75                  80

Phe Thr Val Asp Glu Ile Ile Arg Ala Glu Arg Tyr Met Leu Met Leu
                85                  90                  95

Leu Asp Phe Asp Ile Ser Trp Pro Gly Pro Met Ser Phe Leu Arg Arg
            100                 105                 110

Ile Ser Arg Ala His Ser Tyr Asp His Asp Ile Arg Met Leu Ala Lys
        115                 120                 125

Tyr Leu Gln Glu Val Thr Leu Met Asp Glu Ile Phe Ile Gly Ala His
130                 135                 140

Ile Ser Phe Ile Ala Ala Thr Ala Tyr Tyr Leu Ser Met Gln Met Leu
145                 150                 155                 160
```

```
Gly His Leu Asp Trp Thr Pro Cys His Val Tyr Tyr Ser Gly Tyr Thr
                165                 170                 175

Ala Arg Gln Leu Lys Pro Cys Ala Asn Ile Ile Trp Glu Cys Leu Val
            180                 185                 190

Asp Ala Pro Asn His His Asn Ala Ile Tyr Arg Lys Tyr Ser Glu Asn
        195                 200                 205

Arg Met Lys Arg Val Ser Ala Phe Ala His Asn Trp Val Leu Ser
    210                 215                 220

<210> SEQ ID NO 7
<211> LENGTH: 249
<212> TYPE: PRT
<213> ORGANISM: Homo sapiens

<400> SEQUENCE: 7

Met Thr Ala Arg Leu Arg Asp Phe Glu Val Lys Asp Leu Leu Ser Leu
1               5                   10                  15

Thr Gln Phe Phe Gly Phe Asp Thr Glu Thr Phe Ser Leu Ala Val Asn
            20                  25                  30

Leu Leu Asp Arg Phe Leu Ser Lys Met Lys Val Gln Pro Lys His Leu
        35                  40                  45

Gly Cys Val Gly Leu Ser Cys Phe Tyr Leu Ala Val Ala Ser Ile Glu
    50                  55                  60

Glu Glu Arg Asn Val Pro Leu Ala Thr Asp Leu Ile Arg Ile Ser Gln
65                  70                  75                  80

Tyr Arg Phe Thr Val Ser Asp Leu Met Arg Met Glu Lys Ile Val Leu
                85                  90                  95

Glu Lys Val Cys Trp Lys Val Lys Ala Thr Thr Ala Phe Gln Phe Leu
            100                 105                 110

Gln Leu Tyr Tyr Ser Leu Leu Gln Glu Asn Leu Pro Leu Glu Arg Arg
        115                 120                 125

Asn Ser Ile Asn Phe Glu Arg Leu Glu Ala Gln Leu Lys Ala Cys His
    130                 135                 140

Cys Arg Ile Ile Phe Ser Lys Ala Lys Pro Ser Val Leu Ala Leu Ser
145                 150                 155                 160

Ile Ile Ala Leu Glu Ile Gln Ala Gln Lys Cys Val Glu Leu Thr Glu
                165                 170                 175

Gly Ile Glu Cys Leu Gln Lys His Ser Lys Ile Asn Gly Arg Asp Leu
            180                 185                 190

Thr Phe Trp Gln Glu Leu Val Ser Lys Cys Leu Thr Glu Tyr Ser Ser
        195                 200                 205

Asn Lys Cys Ser Lys Pro Asn Val Gln Lys Leu Lys Trp Ile Val Ser
    210                 215                 220

Gly Arg Thr Ala Arg Gln Leu Lys His Ser Tyr Tyr Arg Ile Thr His
225                 230                 235                 240

Leu Pro Thr Ile Pro Glu Met Val Pro
                245

<210> SEQ ID NO 8
<211> LENGTH: 249
<212> TYPE: PRT
<213> ORGANISM: Homo sapiens

<400> SEQUENCE: 8

Met Thr Ala Arg Leu Arg Asp Phe Glu Val Lys Asp Leu Leu Ser Leu
1               5                   10                  15
```

-continued

```
Thr Gln Phe Phe Gly Phe Asp Thr Glu Thr Phe Ser Leu Ala Val Asn
            20                  25                  30

Leu Leu Asp Arg Phe Leu Ser Lys Met Lys Val Gln Pro Lys His Leu
        35                  40                  45

Gly Cys Val Gly Leu Ser Cys Phe Tyr Leu Ala Val Lys Ser Ile Glu
    50                  55                  60

Glu Glu Arg Asn Val Pro Leu Ala Thr Asp Leu Ile Arg Ile Ser Gln
65                  70                  75                  80

Tyr Arg Phe Thr Val Ser Asp Leu Met Arg Met Ala Lys Ile Val Leu
            85                  90                  95

Glu Lys Val Cys Trp Lys Val Lys Ala Thr Thr Ala Phe Gln Phe Leu
            100                 105                 110

Gln Leu Tyr Tyr Ser Leu Leu Gln Glu Asn Leu Pro Leu Glu Arg Arg
            115                 120                 125

Asn Ser Ile Asn Phe Glu Arg Leu Glu Ala Gln Leu Lys Ala Cys His
    130                 135                 140

Cys Arg Ile Ile Phe Ser Lys Ala Lys Pro Ser Val Leu Ala Leu Ser
145                 150                 155                 160

Ile Ile Ala Leu Glu Ile Gln Ala Gln Lys Cys Val Glu Leu Thr Glu
                165                 170                 175

Gly Ile Glu Cys Leu Gln Lys His Ser Lys Ile Asn Gly Arg Asp Leu
            180                 185                 190

Thr Phe Trp Gln Glu Leu Val Ser Lys Cys Leu Thr Glu Tyr Ser Ser
            195                 200                 205

Asn Lys Cys Ser Lys Pro Asn Val Gln Lys Leu Lys Trp Ile Val Ser
    210                 215                 220

Gly Arg Thr Ala Arg Gln Leu Lys His Ser Tyr Tyr Arg Ile Thr His
225                 230                 235                 240

Leu Pro Thr Ile Pro Glu Met Val Pro
                245
```

MUTATED CYCLIN G1 PROTEIN

This application claims the benefit under 35 U.S.C. 119(e) of provisional application Ser. No. 60/325,765, filed Mar. 2, 2000 now abandoned, the disclosure of which is incorporated by reference in its entirety.

This invention relates to the treatment of pathological conditions and diseases involving abnormal cellular proliferations, such as tumors, cancers, restenosis, hyperplasias, corneal haze and cataracts by providing mutated cyclin G1 protein to an affected animal, thereby inhibiting the function of native cyclin G1 protein. More particularly, this invention relates to the treatment of such conditions and diseases by administering to the animal an expression vehicle, such as a retroviral vector or an adenoviral vector, which comprises a polynucleotide encoding mutated cyclin G1 protein.

BACKGROUND OF THE INVENTION

Genes encoding a new class of proteins known as cyclins have been identified as a new class of protooncogenes, and cyclin-dependent kinase (or Cdk) inhibitors have been identified as tumor suppressors, thereby uniting the molecular mechanisms of cellular transformation and tumorigenesis with the enzymology governing cell cycle control. (Hall, et al., *Curr. Opin. Cell Biol.*, Vol. 3, pgs. 176–184 (1991); Hunter, et al., *Cell*, Vol. 79; pgs. 573–582 (1994); Elledge, et al., *Curr. Opin. Cell Biol.*, Vol 6, pgs. 874–878 (1994); Peter, et al., *Cell*, Vol. 79, pgs. 181–184 (1994)). The sequential expression of specific cyclins and the essential functions of specific Cdk complexes have been defined (Wu, et al., *Int. J. Oncol.*, Vol. 3, pgs. 859–867 (1993); Pines, et al., *New Biologist*, Vol. 2, pgs. 389–401 (1990); Pines, *Cell Growth and Differentiation*, Vol. 2, pgs. 305–310 (1991); Reed, *Ann. Rev. Cell Biol.*, Vol. 8, pgs. 529–561 (1992); Sherr, *Cell*, Vol. 79, pgs. 551–555 (1994)), thereby providing direct links to the fundamental mechanisms of DNA replication, transcription, repair, genetic instability, and apoptosis. (D'Urso, et al., *Science*, Vol. 250, pgs. 786–791 (1990); Wu, et al., *Oncogene*, Vol. 9, pgs. 2089–2096 (1994); Roy, *Cell*, Vol. 79, pgs. 1093–1101 (1994); Meikrantz, et al., *Proc. Nat. Acad. Sci.*, Vol. 91, pgs. 3754–3758 (1994)).

Metastatic carcinoma is an important target for gene therapy as the disease is associated with poor outcome. Colorectal cancer, for example, is the second leading cause of cancer death in the United States after lung cancer, followed by breast and pancreatic cancer (Silberberg et al., *Cancer Clin.*, Vol. 40, pgs. 9–26 (1990)). Of these carcinomas, pancreatic cancer has the worst prognosis. The median survival of patients with metastatic pancreatic cancer is three to six months and virtually all the patients are dead within a year (Merrick et al., *Gastrenterol. Clin. N. Amer.*, Vol. 19, pgs. 935–962 (1990)). Approximately 40% of patients will have metastatic disease either to the liver or the peritoneal cavity or both at the time of diagnosis. Chemotherapy for metastatic disease is ineffective despite multimodal therapy. Hence, alternative approaches to metastatic carcinoma would be desirable.

Wu, et al., (*Oncol. Reports*, Vol. 1, pgs. 705–711 (1994)), discloses the deduced amino acid sequence and cDNA sequence for human cyclin G1 protein. Wu, et al., also disclose that higher levels of cyclin G1 expression were found in osteosarcoma cells and in Ewing's sarcoma cells than in normal diploid human fibroblasts. Although Wu, et al., state that the overexpression of cyclin G1 protein in human osteosarcoma cells provides a potential link to cancer, Wu, et al., do not disclose the treatment of cancer by interfering with or inhibiting the function of cyclin G1 protein in cancer cells.

Atherosclerosis, a principal cause of both myocardial and cerebral infarction, is responsible for ~50% of all mortality in the United States and Europe (Ross, *Nature*, Vol. 362. pgs. 801–809 (1993); Murray and Lopez, *The Global Burden of Disease*, Harvard University Press, Cambridge, Mass. (1996)). In addition to bypass grafting and endarterectomy, percutaneous transluminal coronary angioplasty (PTCA) has become standard treatment for vascular stenosis (Fitz Gibbon, et al., *Can. J. Cardiol.*, Vol. 12, pgs. 893–900 (1996)). While the success rate of the initial PTCA has increased to well over 90%, the long-term efficacy of the procedure is limited by the eventual development of neointimal hyperplasia and restenosis in ~30–50% of patients (Glagov, *Circulation*, Vol. 89 pgs. 2888–2891 (1994); Schwartz et al., *Am. Coll. Cardiol.*, Vol. 17, pgs. 1284–1293 (1992); Myers et al., *Wound Healing Responses in Cardiovascular Disease*, Weber, ed, Futura Publishing Co., Mt. Kisco, N.Y., pgs. 137–150 (1995); Chen, et al., *J. Clin, Invest.*, Vol 99, pgs. 2334–2341 (1997)), often to such an extent that a second PTCA is necessary (Kirchengast, et al., *Cardiovasc. Res.*, Vol. 39, pgs. 550–555 (1998)). To date, no pharmacological strategy has been sufficiently effective to warrant its widespread use (Herrman et al., *Drugs*, Vol. 46, pgs. 18–52 (1993); De Meyer and Bult, *Vascul. Med.* Vol. 2, pgs. 179–189 (1997)). Thus, the control of neointima formation represents a major goal of contemporary research in vascular biology (Schwartz, et al., *The Intima. Circulation Res.*, Vol. 77, pgs. 445–465 (1995)) and a model system for the development of new molecular medicines (Gibbons, et al., *Science*, Vol. 272, pgs. 689–693 (1996)).

The high degree of complexity and redundancy in growth factor signaling pathways has prompted the examination of conserved cell cycle control pathways in the design of novel cytostatic therapies (Barr and Leiden, *Trends Cardiovasc. Med.*, Vol 4 pg. 57 (1994); Andres, *Int. J. Molecular. Med.*, Vol. 2, pgs. 81–84 (1998); Braun-Dullaeus et al., *Circulation*, Vol. 98, pgs. 82–89 (1998)). Consequently, a number of novel gene therapy approaches to inhibit SMC proliferation and neointima formation have focused on specific cell cycle control elements, including oligodeoxynucleotides representing antisense constructs of cyclin-dependent protein kinase (CDK) subunits (Morishita et al., *Proc. Nat. Acad. Sci.*, Vol. 90, pgs. 8474–8478 (1993), Morishita, et al. *J. Clin. Invest.*, Vol. 93. pgs. 1458–1464 (1994); Abe, 1994), adenoviral vectors bearing Cdk inhibitors (Chang et al., *Science*, Vol. 267, pgs. 518–522 (1995); Chen et al., 1997;) or vectors bearing constitutively active forms of the Rb protein (Chang et al., *J. Clin. Invest.*, Vol. 96 pgs , 2260–2268 (1995); Smith et al., *Exp. Cell Res.* Vol. 230, pgs. 61–68 (1997)). Other studies have employed molecular "decoy" oligodeoxynucleotide strategies directed against the transcription factor E2F (Morishita, et al., *Proc. Nat. Acad. Sci.*, Vol. 92, pgs. 5855–5859 (1995)), which regulates the induction of multiple cell cycle control genes. The reported efficacy of these experimental approaches supports the concept that, cell cycle control elements which are selectively up-regulated in neointima lesions would represent strategic therapeutic targets.

Recent studies have characterized the up-regulation of cyclin G1, an inducible cell cycle control element (Tamura et al., *Oncogene*, Vol. 8, pgs. 2113–2118 (1993); Wu, et al., 1994; Home, et al., *J. Biol. Chem.*, Vol. 271, pgs. 6050–6061 (1996); Morishita et al., 1995), following balloon catheter injury in rodents (Zhu et al., 2000; submitted) and non-human primates (Kaijin Wu et al., 1999; submitted). Enforced expression of cyclin G1 in transfected cells in vitro accelerates the cell cycle and promotes clonal expansion (Smith et al, *Exp. Cell, Res.* Vol. 230, pgs. 61–68 (1997),) while blockade of cyclin G1 expression by antisense strategies induces cytostasis and cytolysis (Skotzko, et al, *Cancer Res.*, Vol. 55 pgs. 61–68 (1995); Chen, et al., *Hum. Gene Ther.*, Vol. 8, pgs. 1667–1674 (1997); Hung, et al., *Int. J. Pediatr. Hematol. Oncol.*, Vol. 4, pgs. 317–325 (1997).) In the context of SMC proliferation, it has been shown (i) that an antisense cyclin G1 retroviral vector concentrated to sufficiently high titer ($10^8$ cfu/ml) inhibited the survival and proliferation of transduced rat (Zhu, et al., *Circulation*, Vol. 46 pgs., 628–635 (1997)) and primate vascular SMCs (unpublished observations), and (ii) that intraluminal delivery of this concentrated antisense cyclin G1 vector in balloon-injured rat carotid arteries produced a significant reduction in neointima formation in vivo (Zhu, et al., 1997). Therefore, cyclin G1 appears to be both a pertinent and advantageous locus for therapeutic intervention in the management of vascular restenosis.

SUMMARY OF THE INVENTION

Applicants have discovered that by interfering with and/or inhibiting the function of cyclin G1 protein in cancer cells, one may inhibit, prevent, or destroy the growth and/or survival of such cancer cells. Thus, the present invention is directed to the treatment of pathological conditions and diseases involving abnormal cellular proliferations by inhibiting the function of cyclin G1 protein, through the administration of mutant cyclin G1 proteins to such proliferating cells in an animal. Such pathological conditions and diseases include, but are not limited to, cancers, tumors, hyperplasias, restenosis, corneal haze, and cataracts. In preferred embodiments, the mutant or variant cyclin G1 protein is administered to the affected animal by delivery of expression vehicles comprising polynucleotides encoding mutated cyclin G1 proteins. Such expression vehicles include, but are not limited to viral vectors such as retroviral vectors and adenoviral vectors, and synthetic vectors. Animals that can be treated beneficially by the methods of the invention include, but are not limited to, mammals, including human and non-human primates, dogs, cats, horses, cattle, and sheep.

BRIEF DESCRIPTION OF THE DRAWINGS

The invention now will be described with respect to the drawings, wherein:

FIG. 4 The human cyclin G1 sequence is (SEQ ID NO:3) shown in comparison with those of human cyclin I (SEQ ID NO:4), human cyclin A (SEQ ID NO:5) and S. Pom Cig1 (SEQ ID NO:6). Conserved regions are indicated by gray boxes.

FIG. 5 Schematic diagram of pRES, antisense and mutant cyclin G1 constructs. (A) Map and restriction cloning sites of the pREX retroviral expression vector (B) Schematic diagram of antisense cyclin G1 fragments (C) Schematic diagram of mutant cyclin G1 fragments FIG. 6 Cloning of human cyclin G1 cDNA into pREX retroviral expression vector. Diagram shows stepwise cloning of a point mutant cyclin G1 (PM61) (SEQ ID NO:7) into pG1PM61$_A$/REX.

FIG. 8 Transient transfection scheme and virion incorporation of antisense and mutant cyclin G1 vectors displaying a matrix-targeting motif and a VSVG protein in dual envelope configuration. (A) Retroviral stocks were generated using a transient four plasmid co-transfection system (Soneoka et al., 1995) in which the packaging components gag-pol, the matrix-targeted (CBD) env, the fusogenic VSVG env, and a retroviral vector bearing a cyclin G1 construct, each expressed from the CMV promoter were placed on separate plasmids, each containing the SV40 origin of replication. (B) Western analysis shows the MLV-based gp70 env protein as an immunoreactive band migrating to the region of ~70 kDa, the VSVG protein, at 64 kDa, and the viral gag (CA) protein control, between 36 and 50 kDa. Mock=no envelope control; CAE 109 control=non-targeted null vector with WT MLV env; Hs2+VSVG 109 control=matrix-targeted null vector with a MLV env displaying a collagen-binding motif and VSVG protein in dual env configuration; CAE 587=non-targeted antisense cyclin G1-587 vector with WT env; Hs2+VSVG 587=matrix-targeted VSVG pseudotyped antisense cyclin G1-587; CAE 693=non-targeted antisense cyclin G1-693 vector with WT env; Hs2+VSVG 693=matrix-targeted VSVG pseudotyped antisense cyclin G1-693; CAE D/N (41-249)=non-targeted mutant D/N (41-249) vector with WT env; Hs2+VSVG D/N (41-249)=matrix-targeted VSVG pseudotyped mutant D/N (41-249) vector.

FIG. 10 Western blot analysis of cyclin G1 expression in monkey and rat A10 cells transduced with mutant cyclin G1 vectors. Cellular proteins of transduced cells at 12, 24, and 48 hours after transduction were compared with the cells transduced with the null control vector. (A) Decreased expression of immunoreactive human cyclin G1 protein in monkey SMC cultures transduced with an antisense cyclin G1-693 retroviral vector compared to null vector (Vector) (B) Appearance of immunoreactive mutant human cyclin G1 (p20 mutant) at 20 kDa in rat A10 cell cultures 24 and 48 hours after transduction with the dnG1 retroviral vector, which was absent in cells transduced with the control vector (Vector).

(B) Saline; (C) Null Vector and (D) dnG1 vector.

Figure 13:
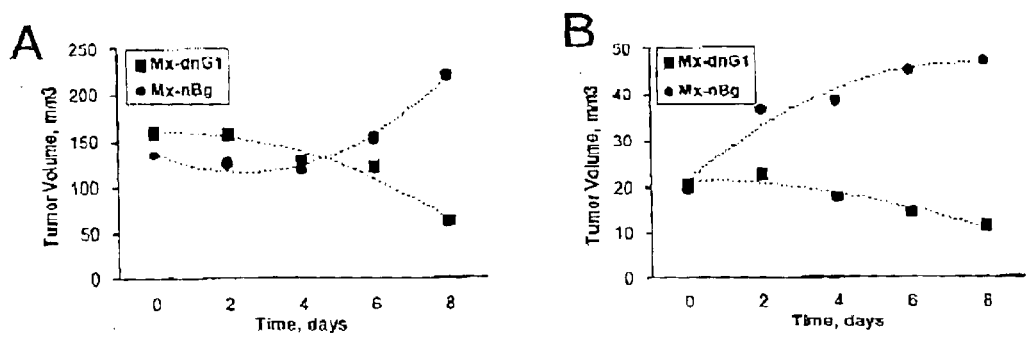

FIG. 13 Arrest of tumor growth with one (7-day) treatment cycle of the Mx-dnG1 vector. The cytocidal vector was injected directly into the tail vein daily for a total of 7 days. The animals were sacrificed on the 8th day after measurements of tumor volumes were obtained using a Vernier caliper. Note that the tumor volumes at the start of treatment of animals in FIG. 13A was considerably greater than those in FIG. 13B. However, in both experiments, appreciable decreases in tumor size were observed by the 4th day of treatment with the Mx-dnG1 vector (n=6), while a progressive increase in tumor size was noted in animals treated with the control Mx-nBg vector (n=4). Tumor volume (mm$^3$; plotted on the vertical axis), was expressed as a function of time (days; plotted on the horizontal axis).

Figure 14:
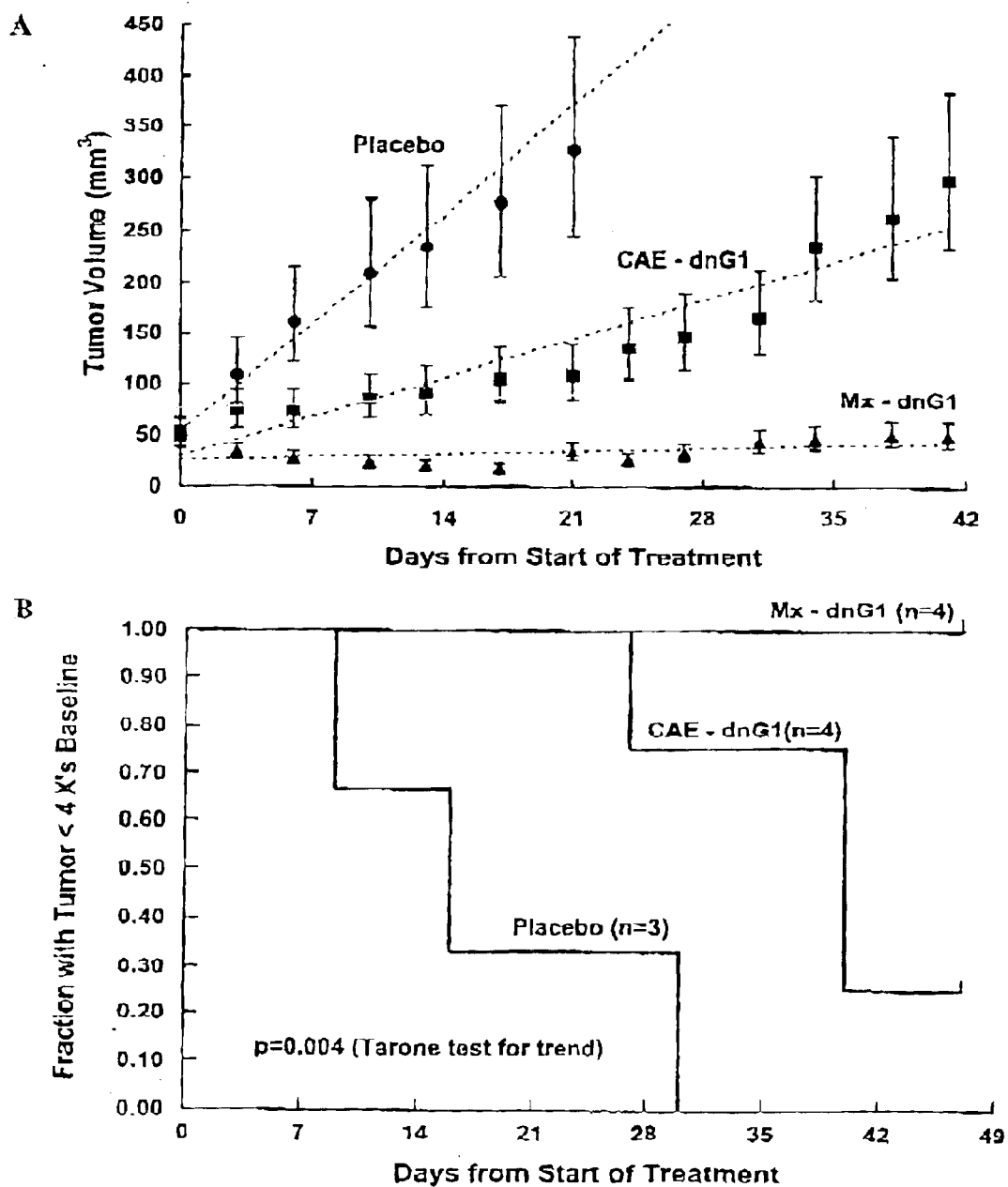

FIG. 14(A) Long term efficacy studies using the Mx-dnG1 vector. Mice bearing established tumor xenografts (tumor volume ~50 mm3) were randomized to receive either placebo (PBS; n=3), a non-targeted CAE-dnG1 vector (n=4) or a matrix-targeted Mx-dnG1 vector (n=4). 200 µl vector (vector dose: 8×10$^6$ cfu) or an equivalent volume of placebo was directly injected into a peripheral (dorsal tail) vein daily or every other day for 10 doses (one treatment cycle) (placebo group) or for two treatment cycles (CAE-dnG1 or Mx-dnG1 groups), with an interim rest period of 2 weeks. Tumor volume (mm3; plotted on the vertical axis), is expressed as a function of time (days; plotted on the horizontal axis). (B) Kaplan-Meier survival studies in mice treated with the Mx-dnG1 vector. The Kaplan-Meier survival curve (representing the time to tumor quadrupling as the endpoint) of animals in (A) is shown. The placebo group is represented by a continuous line; CAE-dnG1 group, by a short dashed line; Mx-dnG1 group, by a long dashed line. The fraction surviving (representing animals with tumors that have not quadrupled; plotted on the vertical axis) is expressed as a function of time (days; plotted on the horizontal axis).

DETAILED DESCRIPTION OF THE INVENTION

In accordance with an aspect of the present invention, there is provided a method of treating an animal affected by a pathological condition or disease involving abnormal cellular proliferation. Such conditions and diseases include tumors, cancers, hyperplasias, restenosis, corneal haze, and cataracts. The method comprises administering to the animal or to the diseased cell, tissue, or organ in the animal a mutated cyclin G1 protein. The mutated cyclin G1 protein is administered in an amount effective to reduce or inhibit the abnormal cellular proliferation, or to ameliorate, cure, or prevent the condition or disease. In a preferred embodiment, the method of the present invention is directed to treating tumors and cancers.

The term "treating a tumor or cancer," as used herein, means that one provides for the inhibition, prevention, or destruction of the growth of the tumor or cancerous cells. Tumors and cancers that may be treated beneficially by the methods of the invention, include, but are not limited to, lymphomas, leukemias, sarcomas, and carcinomas.

The term, "hyperplasia," as used herein, means a non-tumorous pathological condition or disease involving abnormal proliferation of cells in a tissue or organ. Hyperplasias that may be treated beneficially by the methods of the invention include, but are not limited to, angiofollicular mediastinal lymph node hyperplasia, Kimura's disease, angiolymphoid hyperplasia, atypical melanocytic hyperplasia, basal cell hyperplasia, Castleman's disease, hypercementosis, congenital adrenal hyperplasia, congenital sebaceous hyperplasia, congenital virilizing adrenal hyperplasia, cystic hyperplasia, fibromuscular hyperplasia, Heck's disease, intravascular papillary endothelial hyperplasia, neuronal hyperplasia, squamous hyperplasia, and verrucous hyperplasia.

The term "mutated cyclin G1 protein," as used herein, means the native cyclin G1 protein from a eukaryotic organism, but with one or more amino acid deletions, substitutions, additions, and/or combinations thereof. In certain embodiments, the mutated cyclin G1 protein is from an animal. In preferred embodiments, the cyclin G1 protein is from an animal species closely related to the animal being treated (e.g., a mutated chimpanzee cyclin G1 protein being used to treat a human). In a most preferred embodiment, the mutated cyclin G1 protein is from the same animal species as the animal being treated.

The amino acid sequence of human cyclin G1 protein is shown in FIG. 4. In one embodiment, the mutated cyclin G1 protein comprises an amino-terminal truncated cyclin G1 protein. In one embodiment, up to the first 117 amino acid residues at the N-terminal of cyclin G1 protein may be deleted. In a preferred embodiment, the mutated cyclin G1 protein is a cyclin G1 protein comprising an N-terminal deletion up to and including amino acid residue 40. In a most preferred embodiment, the mutated cyclin G1 protein is a human cyclin G1 protein comprising an N-terminal deletion of amino acid residues 1 through 40. In a specific embodiment, the mutated cyclin G1 protein consists of amino acid residues 41 to 249 of human cyclin G1 protein.

In other embodiments, the mutated cyclin G1 protein is a full length or truncated cyclin G1 protein comprising an amino acid substitution at the amino acid residue that corresponds to residue 61 of the human cyclin G1 protein. In preferred embodiments, the mutated cyclin G1 protein has an alanine substitution at that residue. In specific embodiments, the mutated cyclin G1 protein is a full length or truncated human cyclin G1 protein having a lysine or alanine substitution at residue 61.

The mutated cyclin G1 protein may be prepared by techniques known to those skilled in the art. For example, the mutated cyclin G1 protein may be prepared by an automated peptide or protein synthesizer. Alternatively, the mutated cyclin G1 protein may be prepared by genetic engineering techniques.

In one embodiment, the mutated cyclin G1 protein is administered to the animal or directly to the cells, tissue, or organ manifesting the pathological condition or disease by delivery of a polynucleotide comprising a gene construct encoding the mutated cyclin G1 protein. Preferably, the polynucleotide comprises an appropriate expression vehicle.

The term "polynucleotide," as used herein, means a polymeric form of nucleotide of any length, and include ribonucleotides and deoxyribonuceotides. Such term also includes single and double stranded DNA, as well as single and double stranded RNA. The term also includes modified polynucleotides such as methylated or capped polynucleotides.

The gene construct encoding the mutated cyclin G1 protein comprises a sequence encoding the mutated cyclin G1 protein operatively associated with a suitable promoter. According to the invention, a suitable promoter may be any that is active in the treated animal. In preferred embodiments, the promoter is one that is highly active in and/or specific to the abnormally proliferating cells. It is to be understood, however, that the scope of the present invention is not to be limited to specific promoters. In a specific embodiment, the promoter is a cyclin G1 promoter. The sequence encoding the mutated cyclin G1 protein may comprise a native cyclin G1 gene sequence having the desired mutation(s) or a synthetic sequence that encodes the mutated cyclin G1 protein.

The polynucleotide comprising the mutated cyclin G1 gene construct, in a preferred embodiment, is contained in an appropriate expression vehicle which is transduced into the abnormally proliferating cell. Such expression vehicles include, but are not limited to, plasmids, eukaryotic vectors, prokaryotic vectors (such as, for example, bacterial vectors), and viral vectors.

In one embodiment, the vector is a viral vector. Viral vectors which may be employed include RNA virus vectors (such as retroviral vectors) and DNA virus vectors (such as adenoviral vectors, adeno associated virus vectors, Herpes Virus vectors, and vaccinia virus vectors). When an RNA virus vector is employed, in constructing the vector, the polynucleotide comprising the mutated cyclin G1 gene construct is in the form of RNA. When a DNA virus vector is employed, in constructing the vector, the polynucleotide comprising the mutated cyclin G1 gene construct is in the form of DNA.

In one embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, myeloproliferative sarcoma virus, and mammary tumor virus. The vector generally is a replication incompetent retrovirus particle. A retroviral vector within the meaning of the invention includes a lentiviral vector, such as, for example, a vector based on the HIV virus or animal lentivirures, such as for example BIV-based vectors. The construction of lentiviral vectors is disclosed inter alia in U.S. Pat. Nos. 5,665,577; 5,994,136 and 6,013,516, which are incorporated herein by reference with respect to their relevant disclosure.

In one embodiment, the retroviral vector may be generated from a retroviral plasmid vector which is derived from Moloney Murine Leukemia Virus and is of the LN series of vectors, which are described further in Bender, et al., *J. Virol.*, Vol. 61, pgs. 1639–1649 (1987) and Miller, et al., *Biotechniques*, Vol. 7, pgs 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. Pat. No. 5,672,510, which is incorporated herein by reference in its entirety.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes a polynucleotide encoding the mutant cyclin G1 protein which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. A polynucleotide encoding a mutated cyclin G1 protein and/or a promoter having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector may include a promoter for expressing a mutated cyclin G1 protein coding sequence. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, cyclin G1, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The retroviral plasmid vector including the polynucleotide comprising the mutated cyclin G1 gene construct is transduced into a packaging cell line including nucleic acid sequences encoding the gag, pol, and env retroviral proteins. Examples of such packaging cell lines include, but are not limited to, the PE501, PA317 (ATCC No. CRL 9078), ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety, or the 293T cell line (U.S. Pat. No. 5,952,225). The vector may transduce the packaging cells through any means known in the art. Such means include, but are not limited to, electroporation, the use of liposomes, and $CaPO_4$ precipitation. Such producer cells generate infectious retroviral vector particles which include the polynucleotide comprising the mutated cyclin G1 gene construct.

Alternatively, there may be generated a retroviral vector particle which includes the polynucleotide comprising the mutated cyclin G1 gene construct, a first retroviral envelope protein free of non-retroviral peptides (which, in one embodiment, may be a wild-type retroviral envelope protein), and a modified retroviral envelope protein, or "escort" protein, in which amino acid residues of the wild-type retroviral envelope protein have been removed and replaced with a targeting protein or peptide that binds to a desired molecule, such as a cellular receptor or extracellular component, such as an extracellular matrix component, for example. Examples of extracellular matrix components to which the targeting protein or polypeptide may bind include, but are not limited to, collagen.

Such a retroviral vector particle may be generated by transducing a packaging cell, such as those hereinabove described, with the retroviral plasmid vector including the polynucleotide encoding the mutated cyclin G1 protein, and an appropriate expression vehicle, such as a plasmid, including a polynucleotide encoding the modified retroviral envelope peptide. The resulting producer cell then generates infectious retroviral vector particles which include the first retroviral envelope protein free of non-retroviral peptides, the modified retroviral envelope protein, and the polynucleotide encoding the mutated cyclin G1 protein.

In another alternative, the retroviral plasmid vector including the polynucleotide comprising the mutated cyclin G1 gene construct is transduced into a packaging cell which includes polynucleotides encoding the gag and pol retroviral proteins, a polynucleotide encoding a first retroviral envelope protein free of non-retroviral peptides, and a polynucleotide encoding the modified retroviral envelope protein. The resulting producer cell generates retroviral vector particles which include the polynucleotide comprising the mutated cyclin G1 gene construct, a first retroviral envelope protein free of non-retroviral peptides, and the modified retroviral envelope protein.

The retroviral vector particles are administered to an affected animal in an amount which is effective to inhibit, prevent, or destroy the abnormally proliferating cells. Although the scope of the present invention is not to be limited to any theoretical reasoning, it is believed that the mutated cyclin G1 protein competes with native cyclin G1 protein for its cyclin-dependent kinase binding partner, thereby inhibiting the function of native cyclin G1 protein in promoting cell division. Administration of the retroviral vector particles may be by systemic administration, such as by intravenous, intraarterial, or intraperitoneal administration, or by direct injection of the retroviral vectors in the tumor. In general, the retroviral vectors are administered in an amount of at least $10^6$ cfu/ml, and in general, such an amount does not exceed $10^{11}$ cfu/ml. Preferably, the retroviral vectors are administered in an amount of from about $10^8$ cfu/ml to about $10^9$ cfu/ml. The exact dosage to be administered is dependent upon a variety of factors including the age, weight, and sex of the animal or patient to be treated, and the size and severity of the diseased tissue (tumor or organ) being treated.

The retroviral vectors also may be administered in conjunction with an acceptable pharmaceutical carrier, such as, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.). The selection of a suitable pharmaceutical carrier is deemed to be apparent to those skilled in the art from the teachings contained herein.

Accordingly, the present invention also provides for the use in medicine of a mutated cyclin G1 protein, the use a gene construct encoding a mutated cyclin G1 protein and the use an expression vehicle comprising such a gene construct of the invention, and for the treatment of tumors and cancer in particular.

Furthermore, the use of a mutated cyclin G1 protein, the use of a gene construct encoding a mutated cyclin G1 protein and the use of an expression vehicle comprising such a gene construct of the invention for the manufacture of a medicament for the treatment of disease, such as for example tumors and cancer, is provided by the present invention.

In another alternative, the retroviral vectors hereinabove described, or a polynucleotide encoding a mutated cyclin G1 protein, may be encapsulated within liposomes. The liposomes, which encapsulate the retroviral vectors or a polynucleotide encoding a mutated cyclin G1 protein, may be administered to a host in conjunction with a pharmaceutical carrier as hereinabove described.

In another alternative, retroviral producer cells, such as those derived from the packaging cell lines hereinabove described, which include a polynucleotide comprising the mutated cyclin G1 gene construct, may be administered to an animal. Such producer cells may, in one embodiment, be administered systemically (e.g., intravenously or intraarterially) at a point in close proximity to the diseased tissue or organ, or the producer cells may be administered directly to the diseased tissue or organ. The producer cell line then produces retroviral vectors including a polynucleotide comprising the mutated G1 gene construct, in vivo, whereby such retroviral vectors then transduce the abnormally proliferating cells of the diseased tissue or organ.

Pathological conditions and diseases which may be treated in accordance with the present invention include non-malignant, as well as malignant, or cancerous tumors. Cancerous tumors which may be treated include, but are not limited to, osteogenic sarcoma and Ewing's sarcoma and other neoplastic disorders in which cyclin G1 is expressed, such as, glioblastoma, neuroblastoma, breast cancer, prostate cancer, leukemias, lymphomas (including Hodgkin's and non-Hodgkin's lymphoma), fibrosarcoma, rhabdomyosarcoma, colon cancer, pancreatic cancer, liver cancers such as hepatocellular carcinoma, and adenocarcinomas.

The above tumor treatments also may be employed in combination with other treatments of tumors, such as, for example, (i) radiation; (ii) chemotherapy; or (iii) the transduction of the tumor cells with a polynucleotide encoding a negative selective marker, such as, for example, a viral thymidine kinase gene, followed by the administration of an interaction agent, such as, for example, ganciclovir, which kills the cells transduced with the polynucleotide encoding the negative selective marker.

In one embodiment, a mutated cyclin G1 protein is administered to a host in accordance with one of the methods hereinabove described. The growth of any tumor cells which contain the agent will be inhibited, prevented or destroyed. In addition, the tumor cells are transduced with a polynucleotide encoding a negative selective marker or "suicide" gene. The polynucleotide encoding the negative selective marker may be contained in an expression vehicle such as those hereinabove described. Once the tumor cells are transduced with the polynucleotide encoding the negative selective marker, an interaction agent is administered to the host, whereby the interaction agent interacts with the negative selective marker in order to prevent, inhibit, or destroy the growth of the tumor cells.

Negative selective markers which may be employed include, but are not limited to, thymidine kinase, such as Herpes Simplex Virus thymidine kinase, cytomegalovirus thymidine kinase, and varicella-zoster virus thymidine kinase; and cytosine deaminase.

In one embodiment, the negative selective marker is a viral thymidine kinase selected from the group consisting of Herpes Simplex Virus thymidine kinase, cytomegalovirus thymidine kinase, and varicella-zoster virus thymidine kinase. When such viral thymidine kinases are employed, the interaction or chemotherapeutic agent preferably is a nucleoside analogue, for example, one selected from the group consisting of ganciclovir, acyclovir, and 1-2-deoxy-2-fluoro-$\beta$-D-arabinofuranosil-5-iodouracil (FIAU). Such interaction agents are utilized efficiently by the viral thymidine kinases as substrates, and such interaction agents thus are incorporated lethally into the DNA of the tumor cells expressing the viral thymidine kinases, thereby resulting in the death of the tumor cells.

In another embodiment, the negative selective marker is cytosine deaminase. When cytosine deaminase is the negative selective marker, a preferred interaction agent is 5-fluorocytosine. Cytosine deaminase converts 5-fluorocytosine to 5-fluorouracil, which is highly cytotoxic. Thus, the tumor cells which express the cytosine deaminase gene convert the 5-fluorocytosine to 5-fluorouracil and are killed.

The interaction agent is administered in an amount effective to inhibit, prevent, or destroy the growth of the transduced tumor cells. For example, the interaction agent may be administered in an amount from 5 mg to 10 mg/kg of body weight, depending on overall toxicity to a patient. The interaction agent preferably is administered systemically, such as, for example, by intravenous administration, by parenteral administration, by intraperitoneal administration, or by intramuscular administration.

When an expression vehicle, such as those hereinabove described, including a negative selective marker is administered to tumor cells, a "bystander effect" may result, i.e., tumor cells which were not originally transduced with the nucleic acid sequence encoding the negative selective marker may be killed upon administration of the interaction agent. Although Applicants do not intend to be limited to any theoretical reasoning, the transduced tumor cells may be producing a diffusible form of the negative selective marker that either acts extracellularly upon the interaction agent, or is taken up by adjacent, non-transduced tumor cells, which then become susceptible to the action of the interaction agent. It also is possible that one or both of the negative selective marker and the interaction agent are communicated between tumor cells.

Mutated cyclin G1 protein also may be used to prevent vascular restenosis after invasive vascular procedures such as angioplasty, vascular grafts, such as arterial grafts, or coronary bypass surgery. Thus, in accordance with another aspect of the present invention, there is provided a method of preventing restenosis which comprises administering to an animal, or to the site of an invasive vascular procedure or vascular lesion, mutated cyclin G1 protein. The mutated cyclin G1 protein is administered in an amount effective to prevent restenosis in an animal. The mutated cyclin G1 protein may be administered during or after the invasive vascular procedure. The term "invasive vascular procedure" as used herein means any procedure which involves repair, removal, replacement and/or redirection (e.g., bypass or shunt) of a portion of the vascular system including, but not limited to, arteries and veins. Such procedures include, but are not limited to, angioplasty, vascular grafts such as arterial grafts, removals of blood clots, removals of portions of arteries or veins, and coronary bypass surgery.

In a preferred embodiment, the mutated cyclin G1 protein is administered to an animal by transducing vascular cells at the site of an invasive vascular procedure or a vascular lesion with a polynucleotide comprising a mutated cyclin G1 gene construct. Such polynucleotide may be contained in an appropriate expression vehicle as hereinabove described, which is transduced into the cells of the site of an invasive vascular procedure or vascular lesion. In one embodiment, the expression vehicle is a viral vector such as those hereinabove described. In one embodiment, the viral vector is a retroviral vector, which may be as hereinabove described.

When a retroviral vector is employed, such retroviral vector is administered in an amount hereinabove described, and is administered intravascularly. In one embodiment, the retroviral vector is administered to the site of the invasive vascular procedure or the vascular lesion. The vectors transduce the vascular cells at the site of the invasive vascular procedure or vascular lesion, whereby the mutated cyclin G1 protein is produced in such cells, thereby inhibiting the function of native cyclin G1 protein and thus preventing restenosis by preventing the proliferation of such cells.

This method is applicable to the prevention and treatment of restenosis and the prevention or treatment of vascular lesions following a variety of invasive vascular procedures, including, but not limited to, cardiovascular angioplasty, arterial grafts, and coronary bypass surgery. This method also applies to the prevention and treatment of vascular lesions, including, but not limited to, lesions of the femoral, carotid, or renal arteries, particularly renal arteries associated with renal dialysis fistules.

Mutated cyclin G1 protein also may be employed in the prevention and/or treatment of corneal haze or corneal opacity, which is caused in many cases by keratocyte proliferation, and in the treatment and/or prevention of cataracts. Thus, in accordance with another aspect of the present invention, there is provided a method of preventing or treating corneal haze and/or cataracts which comprises administering mutated cyclin G1 protein to the affected animal, or directly to the affected eye. The mutated cyclin G1 protein is administered in an amount effective to prevent or treat corneal haze or cataracts in an animal.

In a preferred embodiment, the mutated cyclin G1 protein is adminstered to the animal by transducing ocular cells with a polynucleotide comprising the mutated cyclin G1 gene construct. Such polynucleotide may be contained in an appropriate expression vehicle as hereinabove described. The expression vehicle is transduced into ocular cells. In one embodiment, the expression vehicle is a viral vector as hereinabove described. In one embodiment, the viral vector is a retroviral vector, which may be as hereinabove described.

When a retroviral vector is employed, such retroviral vector may be administered systemically (intravenously or intraarterially) in an amount of about 10% of blood volume, or from about 500 ml to about 1,000 ml per dose for adults weighing 70 kg or more. The retroviral vector also may be administered to the eye topically such as in the form of eye drops. The retroviral vector also may be administered intraocularly. The vectors transduce ocular cells, such as keratocytes and/or lens epithelial cells, thereby inhibiting the function of native cyclin G1 protein and thus preventing or treating corneal haze or cataracts by preventing the proliferation of keratocytes or lens epithelial cells.

EXAMPLES

The invention now will be described with respect to the examples; however, the scope of the present invention is not intended to be limited thereby.

Example 1

Cytocidal and Cystostatic Effects of a Mutated Cyclin G1 Protein in Cancer Cells.

Materials and Methods

Cells, Cell Culture Conditions, Plasmids and Vectors Bearing Marker and Cell Cycle Control Genes.

NIH3T3, 293T and human pancreatic cancer MiaPaca2 cells were supplied by ATCC. NIH 3T3 and 293T cells were maintained in Dulbecco's modified Eagle's medium supplemented with 10% fetal bovine serum (D10; Biowhittaker). The plasmids pcgp containing the viral gag pol genes, and a retroviral vector, pcnBg, expressing a nuclear targeted β-galactosidase construct were kindly provided by Drs. Paula Cannon and Ling Li respectively (USC Gene Therapy Laboratories, Los Angeles, Calif.). The plasmid containing vesicular stomatitis virus G (VSVG) env protein was kindly provided by Dr. Theodore Friedmann, (University of California, San Diego, Calif.). A truncated (a.a. 41-249) cyclin G1 (dnG1) construct was cloned into the retroviral expression vector pREX.

Production of Matrix-targeted Retroviral Vectors Bearing Mutant Cyclin G1 Constructs. High titer vectors were generated utilizing a transient three or four plasmid co-transfection system, (Soneoka, et al., *Nucl. Acids Res.*, pgs. 628–633 (1995)) in which the packaging components gag-pol, and a chimeric MLV-based env bearing a von Willebrand factor-derived collagen-binding (matrix-targeting) motif expressed from the CMV promoter were placed on separate plasmids, each containing the SV40 origin of replication. The vectors expressed without WT env were named Bv1 or Hs2 (Bv=bovine vWF-derived; Hs=human vWF-derived; LF or 1=linkers derived from natural vWF sequences; LS or 2=standard linkers). To increase viral titer further, a fusogenic VSVG env protein (Yee, et al., Methods Cell Biol., Vol. 43, pgs. 99–112 (1994)) was co-expressed with Bv1 or Hs2 env proteins in a 4 plasmid co-transfection protocol.

Viral Titers in murine NIH3T3 cells were determined as previously described, based on expression of the β-galactosidase or neomycin phosphotransferase resistance, neor, gene (Skotzko, et al., *Cancer Res.*, Vol. 55, pgs. 5493–5498 (1995)). Viral titer was expressed as number of G418 resistant colony forming units (cfu)/ml, and ranged from $10^6$ to $10^8$ cfu/ml, depending on the nature and amount of plasmid DNA used in the transfection protocol.

In vitro Efficacy Studies. To assess the cytocidal/cytostatic effects of the dnG1 vector, the transduced cells were evaluated for their proliferative potential by counting the number of viable cells in each culture at serial intervals (up to 4 days) after transduction without G418 selection. Western analysis of endogenous and mutant cyclin G1 protein expression was performed as described previously (Skotzko, et al., 1995).

In vivo efficacy studies were conducted in compliance with a protocol approved by the University of Southern California Institution Animal Care and Use Committee. To evaluate the efficiency of targeted gene delivery based on the anti-tumor effects of dnG1 vector treatment in vivo, a model of liver metastasis simulating the route of dissemination of human colon cancer was established in nude mice. Briefly, $7 \times 10^5$ tumor cells were infused slowly into the portal vein via an indwelling catheter which was kept in place for 14 days. Intra-catheter infusions of either low or high dose dnG1 vector (titers: $3 \times 10^6$ or $9 \times 10^8$ cfu/ml at 200 μl/day) or an equivalent volume of phosphate buffered saline (PBS, pH 7.4) was begun three days later and continued for a total of 9 days. The mice were sacrificed by cervical dislocation one day after completion of treatment.

Histological and Morphometric Analysis. The liver lobes were excised, fixed in 10% formalin, labeled A for the right and caudate lobes, B for the left lobe and C for the median lobe, processed separately and embedded in paraffin blocks. The anti-tumor efficacy of dnG1 vector treatment was assessed as follows: H & E stained tissue sections were examined by light microscopy, and the surface areas of representative liver sections and tumor foci from lobes A, B and C were measured by morphometric analysis using an Optimas image analysis system. Evaluation of retroviral safety included assessment of the integrity of the liver architecture, examination for presence of hepatocellular swelling or necrosis, inflammatory infiltrates, cholestasis and/or thrombosis. Tissue sections were also immunostained for cytokeratin, human cyclin G1, apoptosis, PAS, vimentin and CD68.

Statistical Analysis. For the in vivo efficacy study, three treatment groups were compared: low dose Bv1/dnG1 (titer: $3 \times 10^6$ cfu/ml), high dose Hs2/VSVG/dnG1 (titer: $9.5 \times 10^8$ cfu/ml) and PBS control. The null vector was not used for in vivo studies based on absence of cytocidal activity in vitro, and since a null vector would not be ultimately used in clinical trials. Initially, eight mice were studied; four were treated with a high dose dnG1 vector, and four, with PBS. Subsequently, four additional mice were treated with a low dose dnG1 vector. The response variables, total surface area (S.A.) of liver, total S.A. of tumor, S.A. tumor to S.A. liver ratio, and mean S.A. tumor foci, were log transformed prior to formal analysis. A repeated measures analysis with lobe as the repeated measures factor was used to determine whether or not the treatment had an effect on each of the response variables. Pair-wise comparisons were also performed for the outcome variables with overall p-values <0.05 between groups.

Results

A mutant human cyclin G1 (dnG1) has been created with a deletion in the cyclin box, a conserved region among cyclins which in part determines cyclin-Cdk association that induces Cdk activation. Preliminary studies demonstrated that dnG1 exhibits anti-proliferative properties in vascular smooth muscle cells. Those findings suggest that dnG1 may act to inhibit the function of wild-type cyclin G1 or form inactive complexes with target Cdk molecules. Hence, the performance of a series of cytocidal mutant cyclin G1 constructs were tested in vitro to determine the optimal construct for further in vivo studies.

Figure 1C:
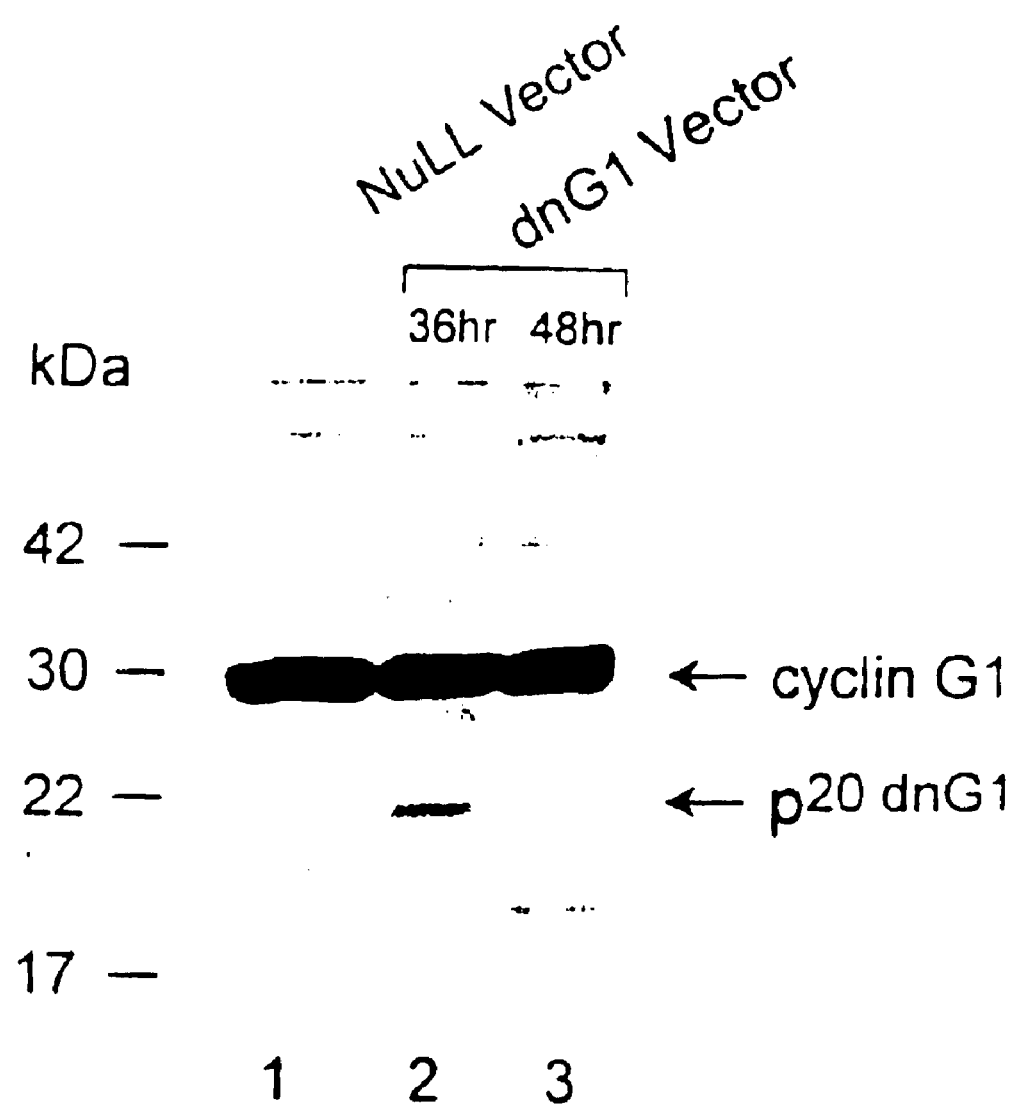
FIG. 1(A) Transduction efficiency of matrix-targeted retroviral vectors in MiaPaca2 cells. β-galactosidase expressing cells are shown with blue-staining nuclei. (B) Cytostatic effects of matrix-targeted retroviral vectors bearing a mutant cyclin G1 constructs in MiaPaca cancer cells. The number of cells per well, plotted on the vertical axis, is expressed as a function of time (days after transduction), plotted on the horizontal axis. D10 Medium control; Null vector bearing only the neo$^r$ gene; AS 587 and AS 693 vectors bearing antisense cyclin G1 constructs; DNT 41 to 249, or dnG1 vector bearing a deletion in the N terminus of human cyclin G1, (C) Western analysis of human cyclin G1 protein expression in dnG1 vector- vs. null vector-transduced cancer cells without G418 selection. Immunoreactive dnG1 (cyclin G1 DN41) is detected as a light staining band in the region of 20 kDa (lane 2), while the endogenous cyclin G1 protein is seen as an intensely staining band in the region of ~30 kDa (lanes 1–3).

A human undifferentiated cancer cell line of pancreatic origin was selected as the prototype of a metastatic gastrointestinal cancer. Retroviral transduction efficiency in these cancer cells was excellent, ranging from 26% to 85%, depending on the multiplicity of infection (4 and 250 respectively; FIG. 1A). For selection of an optimal therapeutic gene, cell proliferation studies were conducted in transduced cells using vectors bearing various cyclin G1 constructs. FIG. 1B shows the cytocidal/cytostatic effects of mutant and antisense cyclin G1 retroviral vectors in transduced cancer cells. Under standard conditions, the dnG1 vector consistently exhibited the greatest anti-proliferative effect, concomitant with the appearance of immunoreactive cyclin G1 at the region of 20 kDa, representing the dnG1 protein (FIG. 1C). Based on these results, the dnG1 vector was selected for subsequent in vivo efficacy studies.

Figure 2:
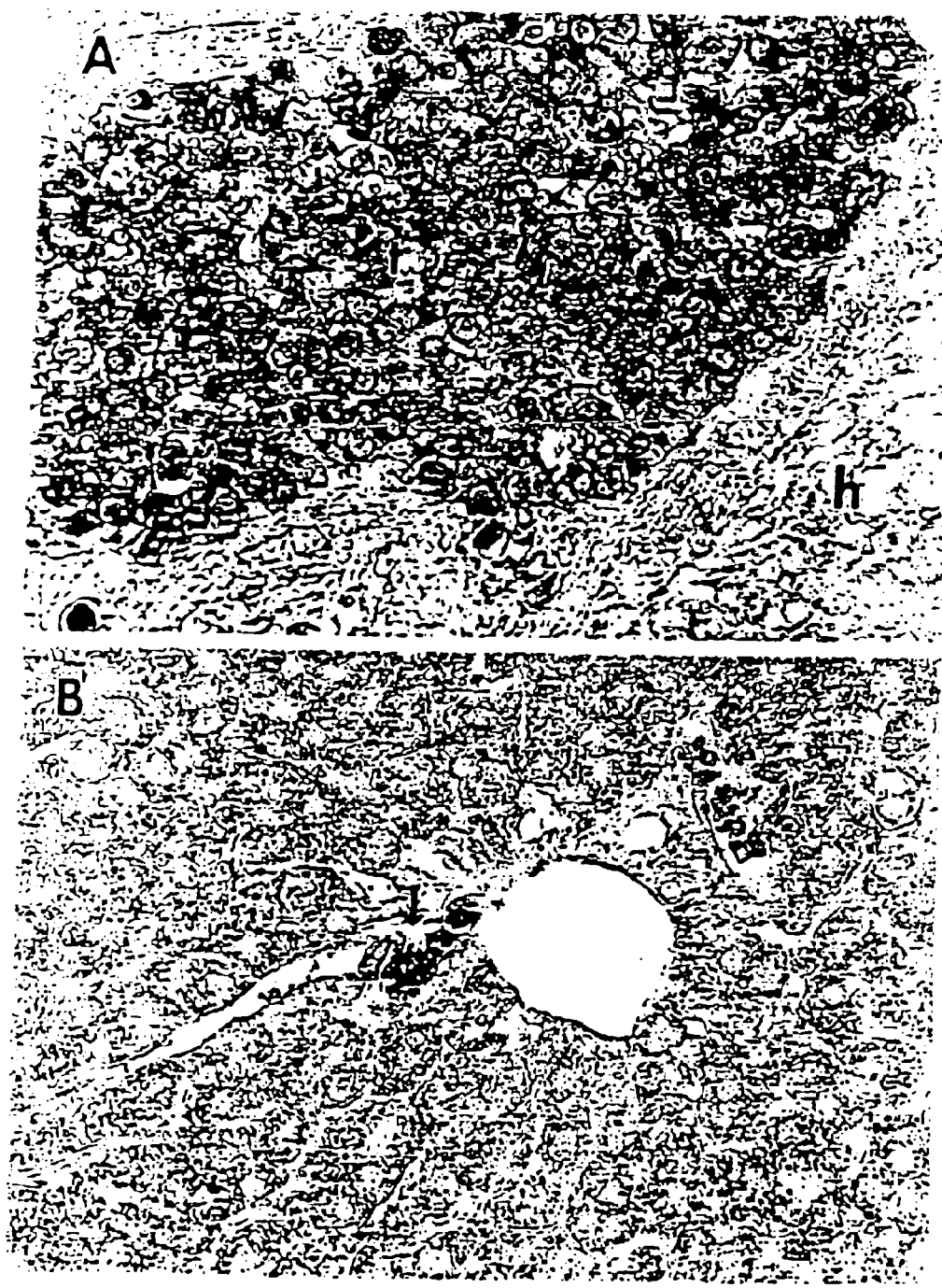
FIG. 2 Human Cyclin G1 Protein Expression in Metastatic Tumor Foci. High level human cyclin G1 protein expression in tumor foci (A; t) of PBS-treated and in residual tumor foci of low dose dnG1-vector treated animals (B; arrow) as evidenced by intense staining of inimunoreactive cyclin G1 with an anti-human cyclin G1 antibody (brown-staining material).
Figure 3A:
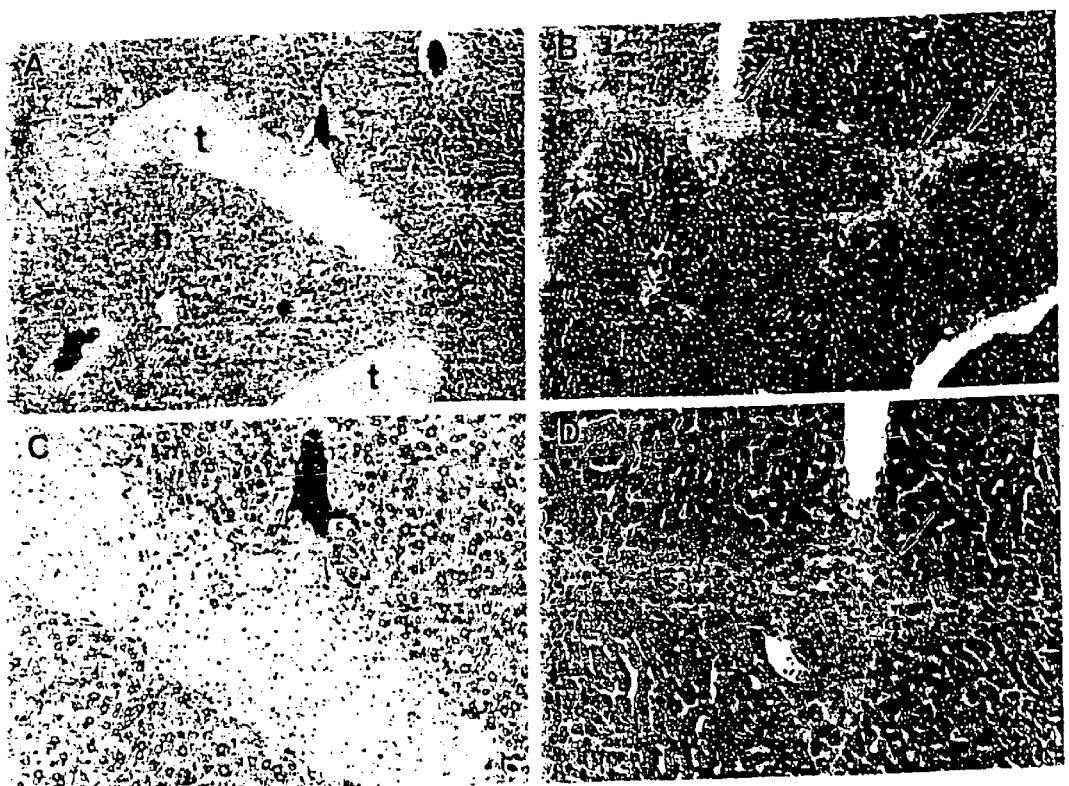
FIG. 3 Hematoxylin-eosin stain of tissue sections of liver reveals the tumor foci from the PBS control group (A & C; 40× and 100×) and the dnG1 vector-treated animals (B & D; 40× and 100×). Apoptosis in tumor foci of the PBS control group (E; 100×), and the dnG1 vector-treated animals (F & H: 100× and 200×; arrows) is depicted as reddish-brown immunostaining material in an ApopTagPlus peroxidase in situ apoptosis assay. (G) Negative staining control without the terminal deoxynucleotidyl transferase TdT enzyme; t=tumor foci; h=hepatocytes in liver parenchyma.
Figure 3B:
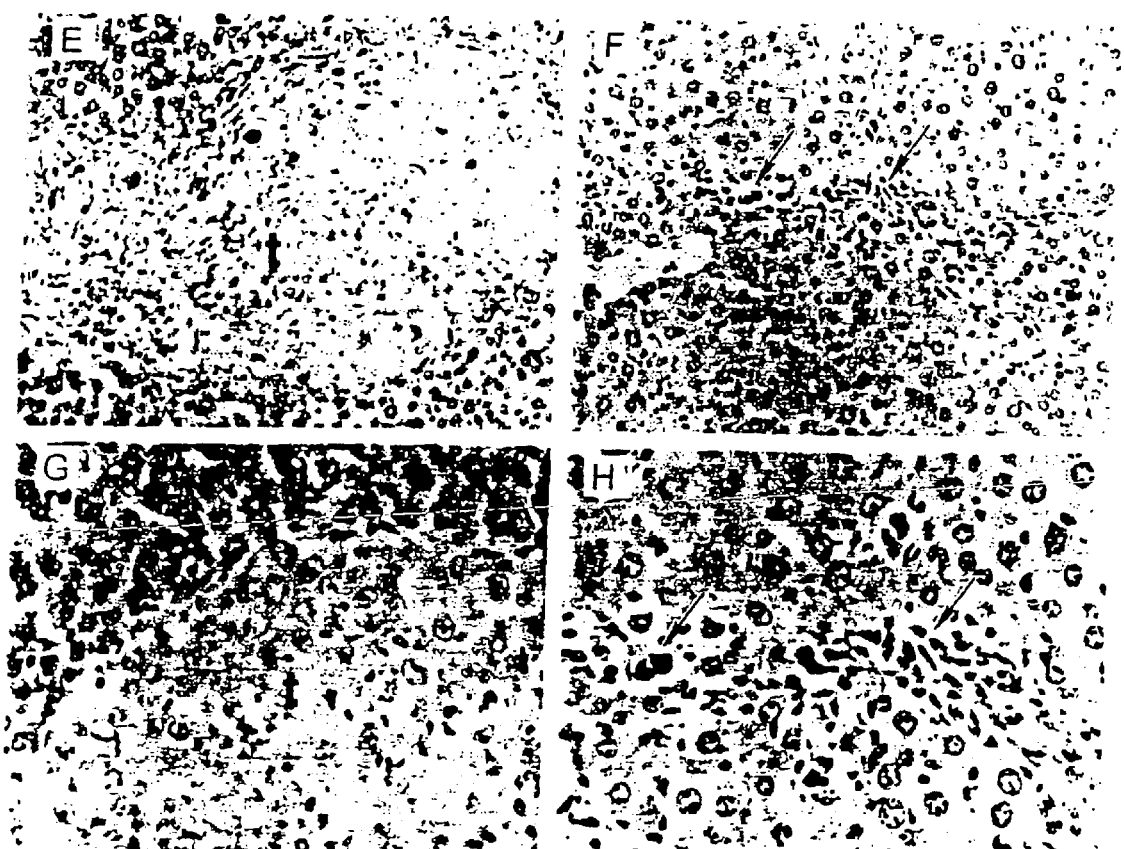

Histologic and immunocytochemical evaluation of metastatic tumor foci from mice treated with either PBS or the low dose dnG1 vector was performed and evaluated with an Optimas imaging system. FIG. 2 shows that the human cyclin G1 protein is highly expressed in metastatic tumor foci, as evidenced by enhanced cyclin G1 nuclear immunoreactivity (brown-staining material) in the PBS-treated animals (FIG. 2A), and in the residual tumor foci (FIG. 2B) of dnG1 vector-treated animals. Histologic examination of liver sections from control animals revealed substantial tumor foci with attendant areas of angiogenesis and stroma formation (FIGS. 3A & C); the epithelial components stained positive for cytokeratin and associated tumor stromal/endothelial cells stained positive for vimentin and FLK receptor (data not shown). In contrast, the mean size of tumor foci in the low dose dnG1-treated animals was significantly reduced compared to PBS controls (FIGS. 3B & D, indicated by arrows; p=0.001), simultaneously revealing a focal increase in the density of apoptotic nuclei (FIGS. 3F & H; indicated by arrows) compared to the PBS control group (FIG. 3E). Further, infiltration by PAS+, CD68+ and hemosiderin-laden macrophages (FIG. 3D; indicated by arrow) was observed in the residual tumor foci of dnG1 vector-treated animals, suggesting active clearance of degenerating tumor cells and tumor debris by the hepatic reticuloendothelial system.

Morphometric analysis of tumor foci confirmed that the targeting strategy for therapeutic gene delivery was effective, in that portal vein infusions (via indwelling catheter) of high dose matrix-targeted dnG1 vectors induced dramatic reductions in the sizes of tumor foci when compared to the control animals based on all response variables (p<0.005; Table I). In pairwise comparisons for the three outcome variables, a dose-dependent tumor response to dnG1 vector treatment was apparent, and additional studies are currently underway to determine better tumor responsiveness to various vector doses in terms of tumor shrinkage vs complete disappearance of the tumor foci and to predict the minimum effective vector dose that could achieve the desired tumor response in Phase I/II gene therapy trials. Importantly, no evidence of hepatocellular damage, necrosis, thrombosis or cholestasis was detected in tissue sections from dnG1 vector-treated animals, indicating that the matrix-targeted dnG1 vector (cumulative dose: $10^6$ to $10^9$ cfu) may have a wide margin of safety.

Discussion

In vivo efficacy and safety studies were conducted in a unique nude mouse model of liver metastasis, and established the proofs of principle that (i) therapeutic gene delivery can be achieved by repeated portal vein infusions (via an indwelling catheter) of matrix-targeted retroviral vectors bearing a cytocidal mutant cyclin G1 construct, as evidenced by statistically significant reductions in the sizes of tumor foci in dnG1 vector-treated mice compared to those of control animals, and (ii) matrix-targeted dnG1 vectors may be systemically administered with a wide margin of safety, as indicated by the absence of associated hepatocyte necrosis, thrombosis or cholestasis. Taken together, these findings represent a definitive advance towards the development of targeted injectable gene therapy vectors for metastatic cancer.

Example 2

Long Term Inhibition of Neointima Formation in Balloon-injured Rat Arteries by Intraluminal Instillation of Matrix-targeted Retroviral Vectors Bearing a Cytocidal Cyclin G1 Construct.

This example demonstrates inhibition of neointinta formation by a mutated cyclin G1 protein in a rat vascular restenosis model.

Materials and Methods

Cells and Cell Culture Conditions

Rat aortic smooth muscle A10 cells (ATCC CRL1476) were maintained as subconfluent monolayers in Dulbecco's modified Eagles medium (DMEM) (Gibco BRL) supplemented with 20% fetal bovine serum (FBS). Mouse embryonic NIH 3T3 cells (ATC CRL 1658), human 293T cells embryonic kidney 293 cells (kindly provided by Dr. Michele Galos, Stanford University, Palo Alto, Calif.) transformed with SV40 large T antigen, and human pancreatic tumor MiaPaca2 cells (ATCC CRL 1420) were maintained similarly in DMEM supplemented with 10% FBS, penicillin, and streptomycin. Primary monkey smooth muscle cells were prepared from harvested left common carotid arteries 7 days after balloon injury, by culture of 2 mm arterial segments in Williams E medium (Gibco BRL) supplemented with 30% FBS. The arterial segments were removed after the cells had migrated and grown as adherent monolayer cells on the tissue culture dish, and the cells were maintained further in Williams E medium –20% FBS. Upon immunostaining with a mouse monoclonal anti-human alpha-smooth muscle actin (DAKO), 95% of cells harvested from the primary culture was positive for smooth muscle alpha actin, indicating their origin.

Plasmid Construction

Cyclin G1 mutant constructs (see FIG. 5), including the 630 bp C-terminal fragment (nucleotides 121 to 750) of cyclin G1 cDNA encoding the amino acids 41 to 249 (Wu et al., 1994) was generated by PCR, cloned into TA vector (Invitrogen), confirmed by sequencing, and re-cloned into pG1XSvNa retroviral vector (Skotzko et al., 1995). The KpnI fragment was obtained by digestion of the resulting construct, containing the retroviral packaging component sequence of pG1XSvNa plus the inserted cyclin G1 cDNA, and was cloned into pRV109 (Soneoka, et al. 1995) to yield the retroviral expression plasmid, pG1DNT41to249/REX, which contains an SV40 origin of replication (ori) and CMV promoter.

Expression plasmids of gag, pol, env, and b-galactosidase proteins—pcgp is a CMV-driven plasmid expressing MLV gag and pa!. pcnBg is an expression construct of β-gal in pREX retroviral vector, generated by stepwise construction in pG1XSvNa and subsequent pRV109 as described (Han, et al., *J. Virol.*, Vol. 71, pgs. 8103–8108 (1997)). Both pcgp and pcnflg were kindly provided by Dr. Paula Cannon (USC Gene Therapy Laboratories, Los Angeles Calif.). The plasmid pCVG is a CMV-driven plasmid expressing vesicular stomatitis virus G glycoprotein (VSV-G) generated by replacing the EcoRI fragment of pCEE+ (MacKrell, et al., *J. Virol.*, Vol. 70, pgs. 1768–1779 (1996)) with the EcoRI fragment of pHCMV-G (a gift from Theodore Friedman, U.C. San Diego) containing the cDNA encoding VSV-G (Yee, et al., 1994). CAEP is a CMV-driven plasmid expressing the amphotropic 4070A (CAE) MLV gp70 containing a matrix-targeting (i.e., collagen-binding domain, CBD) motif. CAEP was generated by inserting a minimal collagen binding domain (WREPGR[M]ELN) (SEQ ID NO:1) derived from human von Willebrand Factor (Takagi, et al., *J. Biol. Chem.*, Vol. 266, pgs, 5575–5579 (1991)) into the retroviral envelope protein at a unique PstI cloning site introduced into the N-terminal domain of the mature protein. A methionine residue (M) was inserted conservatively in place of the wild-type cysteine residue (C) within the minimal CBD, which would otherwise interfere with the appropriate formation of intra-molecular disulfide bonds within the chimeric envelope protein (unpublished data).

Retroviral Vector Production

Human 293T Cells were Plated onto 10 cm Cell Culture dishes at a density of $3 \times 10^6$ cells per dish one day prior to transfection. Transient co-transfections, utilizing 15 mg pcgp, 10 mg pCVG, 5 mg CAEP, and 15 mg either pcnBg or pG1DNT41to249/REX were carried out by the calcium phosphate/DNA co-precipitation method (Soneoka, et al., 1995). The transfected cells were incubated at 37° C. for 16 hours and replaced to 6 ml medium containing 10 mM sodium butyrate to boost the production of viral particles. Approximately 10–12 hours later, the producer cell culture medium was replaced with 8.5 ml of fresh medium and incubated for an additional 24 hours of vector production. The resulting retroviral supernatants were harvested, filtered through 0.45 mM filters, aliquoted, and stored at 70° C. prior to use.

Determination of Retroviral Vector Titers

NIH 3T3 cells were plated onto 6-well culture plates at a density of $2.5 \times 10^4$ cells per well one day before transduction. For cell transduction, serially-diluted retroviral supernatants containing 8 μg/mL polybrene were added to the cell cultures, followed by incubation for 2 hours at 37° C. and subsequent addition of 2 ml fresh medium. 24 hours later, the cells were replaced with fresh medium containing 800 μg/ml G418 and the medium was replaced every 3 days. The G418 resistant colonies were counted 10 days post-transduction by fixing in 10% formalin and staining with 1% methylene blue in 100% methanol. Retroviral vector titers were determined by multiplying the total number of viable colonies by the dilution folds of the retroviral supernatants that were applied to the respective cell cultures.

Determination of Transduction Efficiency in Rat A10 Cells

A10 SMCs were plated onto 6-well culture plates at a density of $3 \times 10^4$ cells per well one day before transduction. Serially-diluted retroviral supernatants containing the β-gal expression construct and 8 mg/mL polybrene were added to the cells. 72 hours later, cells were fixed in 2% formaldehyde, 0.2% glutaraldehyde and stained with 4 mM potassium ferricyanide, 4 mM ferrocyanide, 2 mM MgCl2, and 400 mg/mL of X-gal. Transduction efficiencies were determined by the percentages of cells exhibiting blue-staining nuclei.

Cell Proliferation Assays in Vector-transduced Cell Cultures

A10 cells were plated onto 12-well culture plates at a density of $1.4 \times 10^4$ cells per well. After attachment and incubation overnight, the cells were incubated in 0.5 ml of the respective retroviral supernatants containing 8 μg/mL polybrene at 37° C. for 2 hours, followed by addition of 1 mL fresh medium. The number of viable cells in each treatment group (prepared in triplicate) were determined on consecutive days following cell transduction. Monkey SMCs and MiaPaca2 cells were plated similarly onto 24-well cell culture plates at a density of $3 \times 10^3$ cells per well. As described above, cells were incubated with 0.2 ml of the retroviral supernatant containing 8 μg/mL polybrene, 0.5 ml fresh medium was added after 2 hours, and the numbers of viable cells were determined by harvesting the cell cultures on successive days.

Antibody Production and Purification—

To generate specific anti-cyclin G1 antibodies, a synthetic peptide ([C]KHSYYRITHLPTIPEMYP) (SEQ ID NO:2) representing 18 residues at the extreme C-terminus of human cyclin G1 was synthesized, conjugated to keyhole limpet. hemocyanin (KLH), and used as an immunogen to raise polyclonal antibodies in rabbits. A cysteine residue [C] was added to the N-terminus of peptide to facilitate single-site conjugation to KLH. Further purification of polyclonal anti-cyclin G1 antibodies from immune rabbit serum was performed by affinity chromatography as follows: Filtered rabbit serum was loaded onto an Affi-Gel 10 column (Bio-Rad) coupled covalently with the cyclin G1 immunizing peptide. After extensive washing, bound antibodies were collected in elution buffer (0.1 mM glycine, pH 2.7) and neutralized by 1:10 dilution with 1 M Tris-HCl (pH 8.0) in PBS. Peak fractions containing affinity purified anti-cyclin G1 antibodies were pooled and stored at −70° C. prior to use.

Western Blot Analysis

Approximately 15 mg of soluble protein obtained as detergent lysates from transduced cells was resolved by SDS-PAGE. The gel was then transferred at room temperature to a polyvinylidene fluoride (PVDF) membrane (Millipore) at 120 mA for 1.5 hours, using a Tris-glycine buffer system (25 mM Tris.HCl, pH 8.3, 192 mM glycine, 15% methanol). The membrane was blocked in 3% bovine albumin in PBS for 1 hour prior to incubation with the primary antibody diluted in Western blotting buffer (1% BSA, 0.05% Tween-20 in PBS, pH 7.4) for 30 minutes. The membranes were washed with PBS three times followed by incubation with alkaline phosphatase conjugated secondary antibodies for 30 minutes. After three additional washes with PBS, an insoluble reaction product was developed in the presence of 0.25 mg/mL 5-bromo-4-chloro-3-indolyl phosphate (BCIP) and 0.5 mg/mL nitroblue tetrazolium (NBT) in substrate buffer (100 mM TrisHCl pH 9.5, 100 mM NaCl, and 5 mM $MgCl_2$).

Retrovirus-mediated Transfer of the Cyclin G1 Mutant Construct in a Rat Carotid Injury Model of Vascular Restenosis In compliance with a gene therapy protocol approved by the USC Institutional Animal Care and Use Committee (IACUC) under general anesthesia (ketamine 100 mg/Kg, rompun 10 mg/Kg), a 2F Intimax arterial embolectomy catheter (Applied Medical Resources Corp) was used to denude the carotid artery endothelium of 350 to 450 g Wistar rats. The catheter was inserted into the carotid artery, which was ligated distally, and passed into the common carotid artery. The balloon was inflated to a diameter of ~7 units (French catheter scale) and passed three times along the carotid artery. After balloon injury, the embolectomy catheter was removed, and the carotid artery was transiently clamped and exposed to the retroviral vectors for 30 minutes. Groups of rats received an infusion of ~30 ml of either saline (n=6), retroviral vectors bearing mutant cyclin G1 construct (n=9), or a control vector (n=8), with one additional group of non-treated rats that served as experimental controls (n=7). The rats were sacrificed precisely 4 weeks later by an overdose of sodium pentobarbital (120 mg/Kg IM). Formalin-fixed sections of both non-treated and vector-treated carotid arteries were stained with Verhoeff's elastin stain, histological sections were examined by light microscopy, and morphometric evaluation of the neointima versus media surface areas was made with using an Optimas image anaslysis system. The extent of intimal hyperplasia is expressed as I:M ratios. The significance of differences between the I:M ratios of non-treated, PBS-treated and vector-treated arteries was determined by a pair wise t test.

Results
Design and Engineering of Cyclin G1 Constructs

Figure 6:
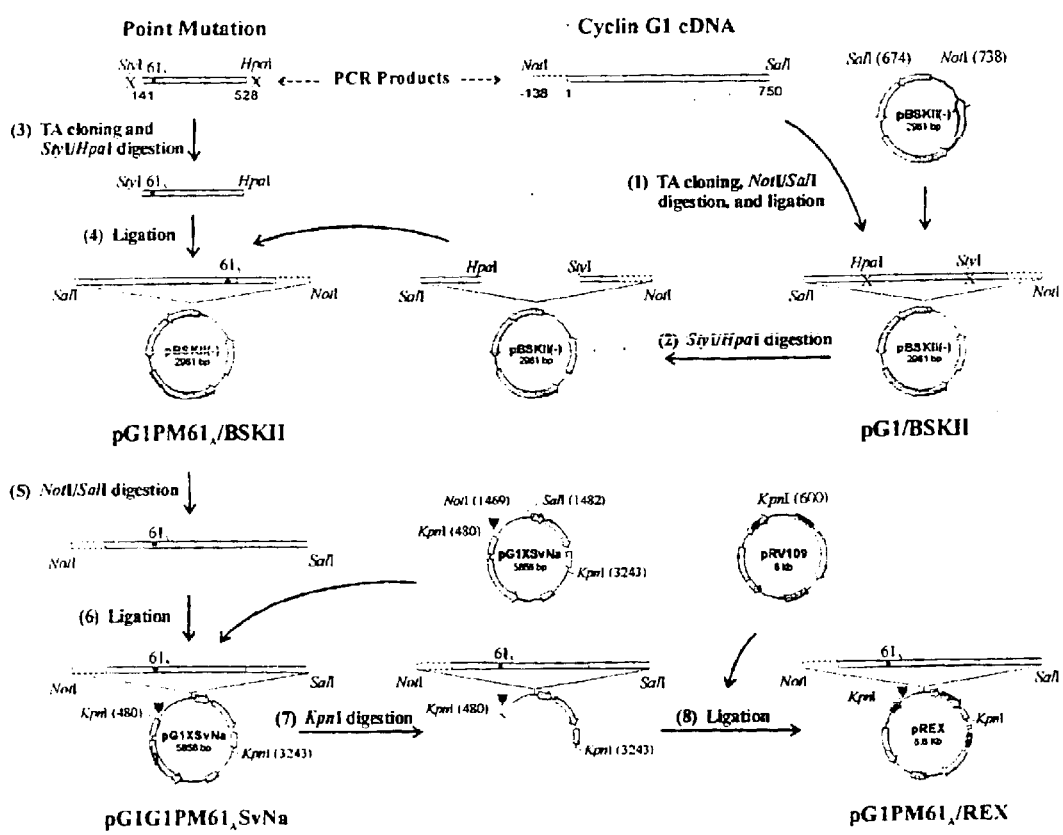

Several antisense fragments derived from human cyclin G1 sequences (FIG. 4), varying in overall length and/or incorporation of upstream sequences, were constructed (FIG. 5). In addition, a series of mutated cyclin G1 expression constructs were engineered and evaluated for their potential to function in a dominant negative fashion. As shown diagrammatically in FIG. 5C, these expression constructs were either mutated or truncated in regions encompassing the conserved "cyclin box" domain, which is implicated in the binding of cyclins to CDKs (Lees and Harlow, *Mol. Cell Biol.*, Vol. 13, pgs. 1194–1201 (1993)). The two point mutants designated PM 61K/A (SEQ ID NO:7) and PM 92E/A (SEQ ID NO:8) respectively, represent modifications of residues that are predicted to be critical for cyclin A-CDK2 contact (Brown et al., *J. Biol. Chen.*, Vol. 267, pgs. 4625–4630 (1992); Jeffrey et al., *Nature*, Vol. 376, pgs. 313–320 (1995)) and are conserved in human cyclin G1 (Wu et al., 1994). Using a complex (eight step) cloning strategy (see FIG. 6), various antisense and mutant cyclin G1 constructs prepared as (NotI/SalI flanked) PCR products were cloned into the NotI/SalI sites of pBSKII (Stratagene) to generate pG1/BSKII constructs, which were subsequently excised and ligated at these cloning sites into a linearized pG1XSvNa retroviral vector (Genetic Therapy, Inc.) to generate pG1G1SvNa constructs. These pG1G1SvNa expression plasmids were digested (at two sites) with KpnI, and the resulting segment of pG1G1SvNa, including the experimental cyclin G1 construct flanked by LTR promoter and Psi encapsidation sequences, was ligated into the pRV109 retroviral vector (Soneoka et al., 1995) to generate the composite retroviral expression vectors pG1/REX. The resulting pG1REX vectors contain a powerful hybrid 5 CMV/LTR promoter driving the therapeutic gene, in addition to SV40 ori sequences and antibiotic resistance genes, which facilitate vector production. The cloning of a representative cyclin G1 point mutant, PM61 K/A into pREX, is shown in FIG. 6.

Comparative Cytostatic Efficacy of the Cyclin G1 Constructs

Figure 7:
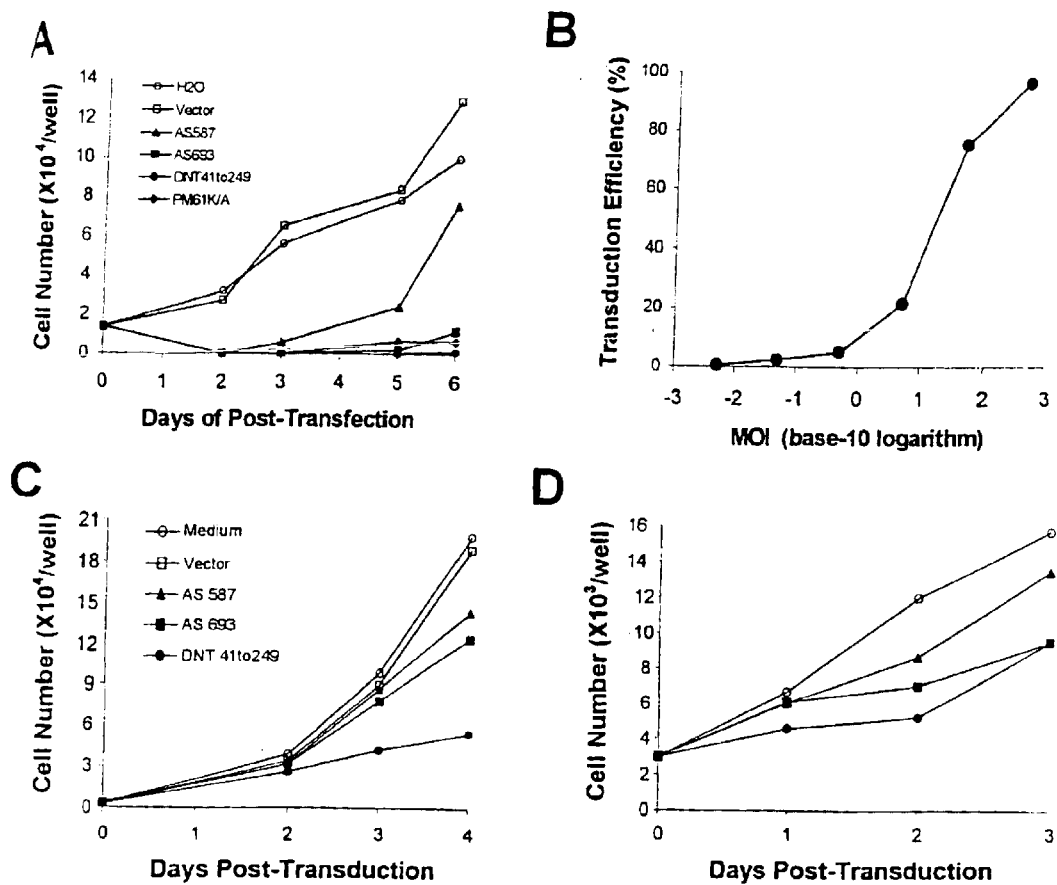
FIG. 7 In vitro studies of plasmid DNA transfection, transduction efficiency and transduction of rat A10 and monkey SMCs with matrix-targeted retroviral vectors bearing marker genes and mutant cyclin G1 constructs. (A) Proliferation of rat A 10 SMCs transfected with mutant cyclin G1 plasmid DNA constructs. Cell numbers, plotted on the vertical axis, are expressed as a function of time, days post-transduction, plotted on the horizontal axis; (B) Transduction efficiency in rat A10 cell cultures following a single two hour transduction using matrix-targeted VSVG pseudotyped retroviral vectors bearing a nuclear-targeted, β-galactosidase gene. Transduction efficiency % is expressed as a function of multiplicity of infection ($_{log}$ MOI); (C) Proliferation of human MiaPaca cells transduced with mutant cyclin G1 retroviral vectors; (D) Proliferation of monkey SMCs transduced with mutant cyclin G1 retroviral vectors.

To examine the comparative effects of the various antisense and mutant cyclin G1 constructs on smooth muscle cell growth, each of the respective DNA fragments was cloned in appropriate orientation into the pREX retroviral expression vector (see above), which was initially employed as a transfectable plasmid for screening studies. Calcium phosphate transfection experiments were performed in triplicate in rat A10 smooth muscle cell cultures to determine the optimal cyclin G1 knock-out constructs for subsequent use in animal studies. In these experiments, the moderate length antisense constructs designated AS587 and AS693 (see FIG. 7A) exhibited greater cytocidal activity than the shorter AS423 construct. Previous studies (with pG1aG1SvNa plasmids) indicated that the full coding sequence of human cyclin G1 in antisense orientation was relatively ineffective (data not shown). Based on these comparative evaluations, AS693, a construct spanning the same coding regions as AS587 (which was previously employed in animal studies: Skotzko et al., 1995, Zhu et al., *Circulation*, Vol. 96, pgs. 628–635 (1997)) yet including additional 5' sequences, was considered to be the most effective antisense design. Among the mutant cyclin G1 constructs tested, one particular mutant construct DNT41 to 249, and a point mutant construct, PM 61K/A, were found to be at least as effective as the antisense constructs in inhibiting smooth muscle cell growth. The efficacy of the point mutant PM 61K/A is interesting in that it suggests that this amino acid, Lys-61, may be critical for the physical association with a presumptive cyclin G1-associated kinase (Smith et al., *Exp. Cell Res.* Vol. 230, pgs. 61–68 (1997)). Based on these comparative screening studies, DNT41-249 and PM 61K/A were also selected for further study.

Characterization of Matrix-targeted Retroviral Vectors Bearing Selected Cyclin G1 Constructs. Retroviral stocks were generated from human 293T cell supernatants, using a transient four plasmid co-transfection system (adapted from Soneoka et al., 1995) in which the packaging components gag-pol, the matrix-targeted (CBD)-env, the fusogenic VSVG env, and a retroviral vector bearing the designated cyclin G1 construct, each driven by the CMV promoter, were placed on separate plasmids (FIG. 8A). Western analysis demonstrated uniform expression of the two envelope proteins in the retroviral producer cells and stable incorporation into viral particles (FIG. 8B), as indicated by the appearance of MLV gp70 env and VSV-G protein immunoreactivity, normalized to the retroviral gag protein in purified vector preparations.

Utilizing this envelope configuration, infectious titers of $10^7$ were achieved routinely, as determined by the expression of neomycin resistance (cyclin G1 constructs) or a β-galactosidase marker gene. To determine the transduction efficiency of the matrix-targeted, VSVG pseudotyped retroviral vectors in rat A10 SMCs, the cells were transduced at various MOIs (ranging from 0.005–500), revealing profound concentration dependence (see FIG. 8B), and indicating that from 75% to 96% of the SMCs were transduced by MOIs from 50 (titer=$3\times10^6$ cfu/ml) to 500 (titer=$3\times10^7$ cfu/ml), respectively, with these matrix-targeted vectors.

Cytotoxicity and Mechanisms of Action of the Cyclin G1 Constructs

Figure 9:
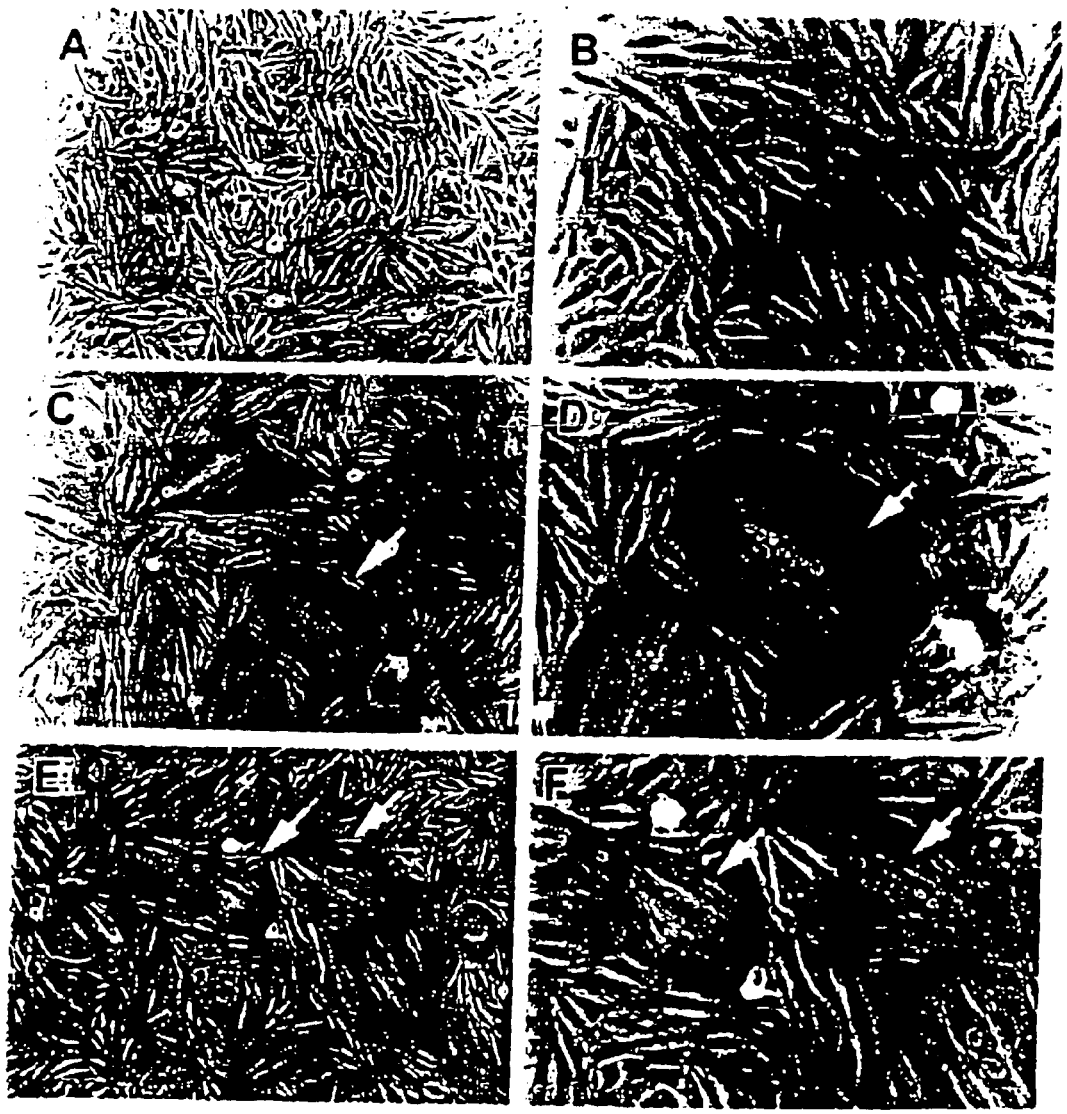
FIG. 9 Syncitia formation in rat A10 cell cultures after transduction with antisense and mutant cyclin G1 retroviral vectors. Photomicrographs display the morphological appearance of rat A10 cells transduced (A & B) Null vector; (C&D) Antisense cyclin G1-693 vector; (D&E) Mutant cyclin G1 (dnG1) vector. The syncitia are indicated by arrows.

Previous studies of retroviral-mediated antisense cyclin G1 cytotoxicity (i.e., AS587) described syncitia formation in transduced cells(Zhu et al., 1997), in addition to cell cycle arrest (Chen, et al., *Hum. Gene Ther.*, Vol. 8, pgs. 1667–1674 (1997)) and overt apoptosis (Zhu, et al., 1997). Remarkably, the cytostatic effects of the mutant cyclin G1 construct also were accompanied by syncitia formation in rat A10 cell cultures observed at t=48 hours after transduction with the pG1DNT41–249/REX vector (FIG. 9), exhibiting large multinucleated cells morphologically similar to those observed with the antisense (AS587 and AS693) constructs. In contrast, neither the control transduction procedures or the null vector (pREX) induced syncitia formation in rat A10 cells (FIG. 9A–B), suggesting that the mutant and antisense constructs affect cell viability in a similar manner. The anti-proliferative effects of the cyclin G1 knock-out constructs were confirmed in human pancreatic cancer cells (FIG. 8C) and in monkey SMCs (FIG. 8D) in which the comparative efficacy of the DNT41-249 expression mutant was again found to be greater than the most potent antisense constructs.

Figure 11:
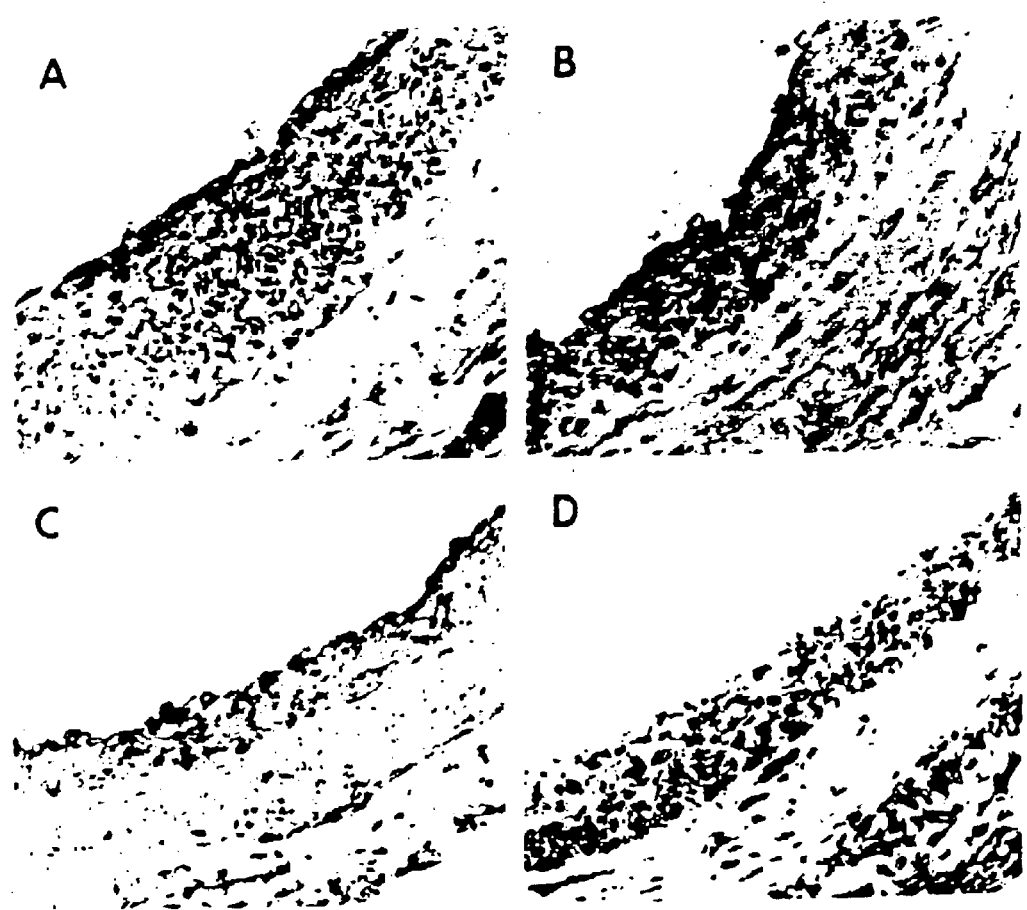
FIG. 11 Immunohistochemical staining of rat cyclin G1 protein in balloon-injured rat arteries. Enhanced cyclin G1 nuclear immunoreactivity (indicated by reddish-brown nuclear staining in neointimal cells of the (A) null vector-(B) PBS and (D) dnG1 vector-treated arterial segments. Decreased intensity of cyclin G1 immunoreactivity in the (C) antisense cyclin G1-693-treated arterial segments.

To substantiate the mechanisms of action of the respective cyclin G1 constructs, the down-regulation of cyclin G1 protein expression was demonstrated by Western analysis of smooth muscle cells transduced with the AS693/REX antisense vector. As shown in FIG. 10A, down-regulation of cyclin G1 expression is observed in monkey SMC cultures transduced with the antisense vector compared to a control vector, with maximum inhibition observed at t=48 hours post-transduction. Conversely, enforced expression of the cyclin G1 mutant construct was verified in A10 cells transduced with the vector (FIG. 10B), as shown by the appearance of an immunoreactive band appropriately at ~20 kDa in transduced cell cultures observed at 24 and 48 hours after transduction with the mutant expression vector. While the demonstration of vector performance in terms of directing protein expression is meaningful, the proportion of cells transiently expressing the predicted (cytotoxic) phenotype at a given time (prior to cell death) may be small. In acute studies of balloon injured arteries in vivo, up-regulation of cyclin G1 protein expression is observed in neointimal SMCs. This characteristic up-regulation of cyclin G1 expression was not diminished in balloon-injured arteries treated with either the null vector (FIG. 11A), the PBS control (FIG. 11B), or the mutant expression vector (FIG. 8D). In contrast, marked down-regulation of cyclin G1 expression was evident in the antisense cyclin G1 (AS693/REX) vector-treated arteries. Taken together, these data indicate that the cytocidal effects of the cyclin G1 constructs results from direct modulation of cyclin G1 expression in transduced cells.

Figure 12:
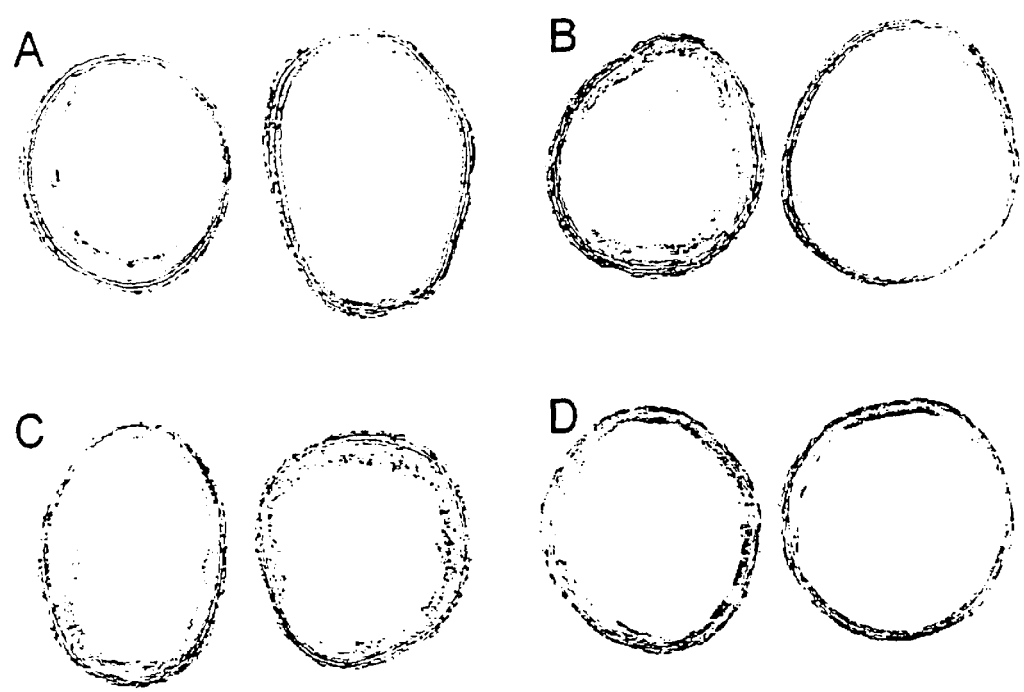
FIG. 12 One-month in vivo efficacy studies using matrix-targeted VSVG pseudotyped dnG1 vectors. Elastin-stained tissue sections from rat carotid arteries harvested one month after balloon-injury and intraluminal instillation of (A) PBS control.

Evaluation of pDNTG1/REX in a Rat Model of Vascular Restenosis. Finally, in two controlled one-month in vivo efficacy studies, intraluminal instillation of a matrix-targeted VSVG pseudotyped vector bearing the N-terminal deletion mutant of cyclin G1 (DNT41-249/REX ) into balloon-injured rat arteries inhibited neointima lesion formation when compared to the null vector, the saline control, and the injured/untreated group (FIG. 12). Unlike the cytotoxic HStk vector (plus ganciclovir) strategy, which produced massive scarring and deformity of the vessel (unpublished observations), there was no evidence of necrosis, fibrosis, or deformation of the arterial wall in the DNT41-249/REX vector-treated arteries, attesting to the relative safety of this approach. Moreover, the long term (30 day) efficacy data (Tables 1 and 2) indicate that little if any "catch-up" of SMC growth developed within the neointimal lesions in the DNT41-249/REX vector-treated animals, suggesting that targeted transduction and expression of a cytocidal cyclin G1 mutant protein in activated SMC may have significant impact on the cellular dynamics responsible for the morbid sequela of vascular restenosis.

TABLE 1

Inhibition of Neointima Lesion Formation Using a Matrix-targeted Retroviral Vector Bearing a Cytocidal Mutant Cyclin G1 Construct in a One-month Efficacy Study

| Treatment Group | Mean Intima:Media Ratio | Confidence Interval | % Inhibition |
|---|---|---|---|
| Injury only | 1.41 | 1.10–1.71 | |
| Saline | 1.24 | 0.92–1.56 | |
| Null vector | 1.25 | 0.92–1.57 | |
| dnG1 vector | 0.62 | 0.28–0.96 | |
| | p = 0.002 vs Injury only | | 56% vs Injury |
| | p = 0.012 vs Saline control | | 50% vs Saline |
| | p = 0.011 vs Null vector | | 50% vs Null |

[1] The intima:media ratios of the control groups (injury alone, saline and null vector) were not significantly different.
[2] The dnG1 vector treated group was compared to three control groups. Pair-wise comparisons were performed for the outcome variable (Intima:Media ratio).

TABLE 2

Inhibition of Neointima Lesion Formation Using a Matrix-targeted Retroviral Vector Bearing a Cytocidal Mutant Cyclin G1 Construct in a One-month Efficacy Study

| Treatment Group | Mean Intima:Media Ratio | Standard Deviation | % Inhibition |
|---|---|---|---|
| Injury only | 1.44 | 0.07 | |
| Saline | 1.39 | 0.15 | |
| Null vector | 1.50 | 0.17 | |
| dnG1 vector | 0.96 | 0.11 | |
| | p = 0.001 vs Injury only | | 33% vs Injury |
| | p = 0.020 vs Saline control | | 31% vs Saline |
| | p = 0.010 vs Null vector | | 36% vs Null |

[1] The intima:media ratios of the control groups (injury alone, saline and null vector) were not significantly different.
[2] The dnG1 vector treated group was compared to three control groups. Pair-wise comparisons were performed for the outcome variable (Intima:Media ratio).

Discussion

The present disclosure demonstrates the utility of using a mutant cyclin G1 protein to inhibit the function of its normal counterpart in a dominant fashion. Such application of a mutated protein has the dual advantages of blocking the finction of closely related (redundant) elements and of producing a detectable gene product (see FIG. 10). Here, one deletion mutant and one point mutant of cyclin G1 exhibited demonstrable anti-proliferative properties which were at least as effectve as the most potent antisense cyclin G1 constructs. The matrix-targeted retroviral vectors bearing a selected mutant cyclin G1 construct (DNT 41-249) was initially tested in vitro, where profound inhibition of cell growth was observed. In a manner comparable to the antisense cyclin G1 constructs (Zhu et al., 1997), the dominant negative cyclin G1 construct produced syncitia formation and unscheduled apoptosis in transduced SMCs, suggesting a mechanistic similarity.

In addition to the therapeutic gene constructs, significant improvements in the efficiency of retroviral-mediated gene delivery to injured arteries was afforded by the incorporation of matrix targeting technology into the viral particles (see below), which served to enhance vector bioavailability. Recent advances in retroviral vector targeting technology have demonstrated that the physiological surveillance function inherent the primary structure of von Willebrand factor (Montgomery et al., *Hemophilia and von Willebrand Disease*, Chapter 44, pgs. 1631–1675, W. B. Saunders Co., Philadelphia (1998); Ginsburg, D, et al., *Proc. Nat. Asal. Sci.* Vol. 86, pgs. 3723–3727 (1989); Ruggeri & Zimmerman, *Blood*, Vol. 70, pgs. 895–904 (1987)) may be adapted to the development of matrix-targeted retroviral vectors (Hall, et al. *Human Gene Therapy*, Vol. 8, pgs. 2183–2192 (1997); Anderson, *Nature*, Vol. 392 (Suppl.), pgs. 25–30 (1998)). The engineering and insertion of a vWF-derived matrix-targeting (i.e. collagen-binding) motif into the retroviral envelope enhances gene delivery in vivo by bestowing the MLV-based vector with a propitious gain-of-function phenotype, i.e., high-affinity binding to extracellular matrix components exposed by balloon catheter injury. The matrix-targeted amphotropic envelopes employed in these studies (see Hall et al., 2000) supersede the original ecotropic (rodent specific) vectors, that were previously shown to accumulate at sites of vascular injury (Hall et al., 1997) and to enable the efficient transduction of resident SMCs in two-week efficacy studies of antisense cyclin G1 (Zhu et al., 2000; submitted). Inasmuch as the activation and proliferation of medial SMCs begins within hours after injury, migration into the neointima occurs by day 4 (Clowes et al. *Lab. Invest.*, Vol. 49, pgs. 327–373 (1983), Clowes et al., *Circ Res.*, Vol. 56, pgs. 139–145 (1985)), and replication increases markedly over the next 2 weeks (Schwartz et al., 1995; DeMeyer and Blut, 1997), vector penetration and cellular transduction was further optimized by intraluminal instillation of the matrix-targeted amphotropic vectors (i) at the time of balloon injury (Zhu et al., 1997) and (ii) seven days post-angioplasty (Hall et al., 2000), when SMC migration and proliferation within the neointima is maximal.

In the present disclosure, a transient transfection system adapted from Soneoka et al., 1995 was used to produce high titer retroviral vectors, wherein the expression of the packaging components, as well as the therapeutic gene, are driven by the powerful CMV promoter; and each of the constructs contain an SV40 origin of replication (ori), which serves to facilitate plasmid expression in human 293T producer cells. Viral titers ranging from $3 \times 10^{6-3 \times 10^8}$ cfu/ml were routinely achieved with these reagents. Moreover, co-expression of the fusogenic VSVG env protein (Iida, et al., *J. Virol.*, Vol. 70, pgs. 6054–6059 (1996); Laitinen, et al., *Hum. Gene Ther.*, Vol. 8, pgs. 1645–1659 (1997); Yu, et al., *Gene Therapy*, Vol. 6, pgs. 1876–1883 (1999)) further improved viral titers (up to $9 \times 10^8$ cfu/ml) without additional vector concentration, thus facilitating vector production and characterization of the prospective therapeutic constructs.

Together, these improvements in retroviral vector design, engineering, and deployment enabled the development of an optimized gene therapy protocol and the achievement of long term efficacy in preventing neointima formation in the rat model of balloon angioplasty (see Table I). In two controlled one-month efficacy studies, the intraluminal delivery of a matrix-targeted dnG1 retroviral vector to the balloon-injured rat carotid artery resulted in ~50% inhibition of neointima lesion formation with no confounding "catch-up" of SMC growth, a magnitude of response induced by only one other drug, a protein kinase C inhibitor (Prescott, et al., *Ann. N.Y. Acad. Sci.*, Vol. 878, pgs. 179–190 (1999)) and an adenoviral vector bearing a nitric oxide synthase construct (Shears, et al., *J. Am. Coll. Surg.*, Vol. 187, pgs. 295–306 (1999)). Unlike HStk vectors (followed by ganciclovir administration), which produces untoward distortion of the arterial histology (Nabel, *Nature*, Vol. 362, pgs. 844–846 (1993)), the apparent absence of necrosis, fibrosis and deformation of arterial wall in dnG1 vector-treated arteries (see FIG. 12) attests to the safety of this approach for in vivo clinical use. In conclusion, this study combines significant improvements in the therapeutic cyclin G1 constructs with advances in matrix targeting technology, vector production methodologies, and instillation protocols to extend the utility of cytocidal gene therapy for the treatment of vascular restenosis.

Example 3

Systemic Administration of a Matrix-targeted Retroviral Vector is Efficacious for Cancer Gene Therapy in Mice Materials and Methods Cells, Cell Culture Conditions, Plasmids and Vectors Bearing Marker and Cell Cycle Control Genes. NIH3T3, 293T and human pancreatic cancer MiaPaca2 cells were supplied by ATCC. NIH 3T3 and 293T cells were maintained in Dulbecco's modified Eagle's medium supplemented with 10% fetal bovine serum (D10; Biowhittaker, Walkersville, Md., USA). The plasmids pcgp containing the viral gag pol genes, and a retroviral vector, pcnBg, expressing a nuclear targeted b-galactosidase construct were kindly provided by Drs. Paula Cannon and Ling Li respectively (USC Gene Therapy Laboratories, Los Angeles, Calif.). A truncated (a.a. 41-249) cyclin G1 (dnG1) construct was cloned into the retroviral expression vector pREX which was modified from pHIT109 (Soneoka et al., Nucl. Acid Res. 23, 628–633. 1995) to contain the retroviral packaging component sequence of G1XSvNa (a gift from Genetic Therapy, Inc., Gaithersburg, Md., USA).

Production of Matrix-targeted Retroviral Vectors Bearing Mutant Cyclin G1 Constructs. High titer vectors were generated utilizing a transient three or four plasmid co-transfection system (Soneoka et al., Nucl. Acid Res. 23, 628–633.1995) in which the packaging components gag-pol, and a chimeric amphotropic Moloney murine leukemia virus (MuLV)-based env bearing a von Willebrand factor-derived collagen-binding (matrix-targeting) motif expressed from the CMV promoter, and a retroviral vector were placed on separate plasmids, each containing the SV40 origin of replication. The vectors are referred to as Mx-nBg, Mx-dnG1 and CAE-dnG1, to indicate the specific envelope used and the gene expression construct incorporated in each vector. Mx-nBg represents a modified MuLV-based vector bearing a matrix-targeting motif in its envelope, and a nuclear-targeted b-galactosidase gene. Mx-dnG1 is a matrix-targeted cytocidal vector bearing an N-terminal deletion mutant cyclin G1 construct (Gordon et al., Cancer Res. 60, 3343–3347. 2000). CAE-dnG1, is a non-targeted vector bearing a wild type amphotropic MuLV-based envelope (Morgan et al., J. Virol. 67, 4712–4721.1993) and the same cytocidal cyclin G1 construct as in Mx-dnG1.

Viral titers in murine NIH3T3 cells were determined as previously described, based on expression of the β galactosidase or neomycin phosphotransferase resistance, neo$^r$, gene (Skotzko et al., Cancer Res. 55, 5493–5498.1995). Viral titer was expressed as number of G418-resistant colony forming units (cfu)/ml, and ranged from $10^7$ to $10^8$ cfu/ml.

In vivo Efficacy Studies. These studies were conducted in compliance with a protocol approved by the University of Southern California Institution Animal Care and Use Committee. To evaluate the efficiency of targeted gene delivery based on the anti-tumor effects of the Mx-dnG1 vector treatment in vivo, subcutaneous tumor xenografts were established in athymic nu/nu mice by subcutaneous implantation of $1-9 \times 10^7$ human MiaPaca2 cancer cells. When the tumors reached a size of 50 mm, 200 μl of either the Mx-dnG1 vector (titer: 8×10⁶ cfu/25 gm mouse), the Mx-nBg control vector of similar titer, a non-targeted CAE-dnG1 vector, or phosphate buffered saline (PBS, pH 7.4) placebo control was injected directly into the tail vein daily for 7–10 days (one treatment cycle). The size of the tumor was measured every 2–4 days with a Vernier caliper, using the formula for calculating the volume of ellipsoid objects: Tumor Volume, $mm^3 = 4/3 \, p \, r_1 \, r_2 \, r_3$. The mice were sacrificed by cervical dislocation one day or one week after completion of one or two treatment cycles, respectively.

Apoptosis Assay. Tissue sections from tumor nodules were evaluated for the induction of apoptosis using the Apoptag kit (Intergen, Purchase, N.Y., USA). Quick frozen tumor nodules were fixed with paraformaldehyde and their membranes permeabilized with ethanol and acetic acid. TdT enzyme was added followed by an anti-didoxygenin peroxidase conjugate. The tissue sections were then stained with a peroxidase substrate and counterstained with methyl green.

Statistical Analysis. (i) To summarize the change in tumor volume over time (rate of tumor growth), a least squares straight line was fit to the log-transformed values; i.e., for each mouse, the slope was estimated using the first 5 measurements over time. These calculated slopes were transformed back into the original scale by taking the anti-logarithm, and represent the average rate of tumor growth (%) per day. To compare the different vectors within each of the three experiments, a weighted analysis of variance was used with the estimated slopes as the dependent variable. For each mouse, the weight was the reciprocal of the sum of the standard error of the estimate slope (as calculated in the initial least squares straight line analysis) plus an estimate of the slope-to-slope variance based on all three experiments. For experiments I and II, the F-test based on the analysis of variance was used to compare the Mx-nBg and Mx-dnG1 vectors, and for experiment III, the F-test followed by least significant difference method of multiple comparisons was used to compare the Mx-dnG1 to the CAE-dnG1 vector and placebo treatments. The combined results of the analyzed data are shown in Table 3. (ii) The Kaplan-Meier product limit method (Kaplan & Meier J. Amer. Statist. Assoc. 53, 457, 1958) was used to estimate the probability of tumor quadrupling as a function of time (days). (iii) The Tarone test for trend (based on the logrank test; Tarone, Biometrika 62, 679, 1975) was used to compare the quadrupling times of the placebo (PBS)-treated, the non-targeted CAE-dnG1 vector-treated, and the matrix-targeted Mx-dnG1 vector-treated groups.

Results

In short-term efficacy studies, intravenous infusions of either the Mx-nBg control vector, the non-targeted CAE-dnG1 vector or the Mx-dnG1 cytocidal vector (each vector= ~8×10⁶ cfu/dose) or an equivalent volume of PBS placebo, commenced six days after implantation of 1–9×10⁷ human MiaPaca2 pancreatic cancer cells, and were continued daily in a subset of mice for a total of 7 vector infusions. Progressive growth in tumor size was observed in mice treated with the Mx-nBg vector (FIG. 13), the non-targeted CAE-dnG1 vector and placebo PBS (Table 3). In contrast, tumor regression was observed in animals that were treated with the Mx-dnG1 vector (FIG. 13; Table 3). Immunohistochemical staining revealed intense nuclear immunoreactivity for the human cyclin G1 protein expressed in the large tumors of control vector-treated mice, while attentuation of cyclin G1 expression was observed in the residual tumors of Mx-dnG1 vector-treated animals.

To evaluate the efficiency of gene delivery into solid tumors by matrix-targeted retroviral vectors, two subsets of animals were sacrificed after seven vector doses had been administered (FIG. 13). Histopathologic examination of hematoxylin & eosin-stained tumor tissue sections from animals treated with the Mx-nBg control vector revealed tumor nodules consisting of a heterogenous population of tumor and tumor-associated cells, i.e., a predominant proportion of malignant epithelioid cells with a relatively high mitotic rate with intervening areas of active angiogenesis surrounded by a thin connective tissue capsule. In contrast, the tumor nodules from the Mx-dnG1 vector-treated animals showed evidence of massive tumor destruction, a high incidence of apoptosis in the remaining tumor cells, and reactive stromal hyperplasia. A number of tumor nodules exhibited large central areas of necrosis, an intermediate zone of active tumor, and a peripheral zone containing an abundance of apoptotic cells. Other resolving tumor nodules were almost completely surrounded by dense connective tissue, which accounted for a considerable proportion of the residual tumors exhibiting small regions of overtly apoptotic cells and varying degrees of acute and chronic inflammation.

Transduction efficiency was determined by immunohistochemical staining of the tumor nodules, using a mouse monoclonal antibody directed against the b-galactosidase antigen (GAL-40, Sigma, St. Louis Mo., USA) followed by analysis using an Optimas imaging system (Optimas Corporation, Bothell, Wash., USA). Transduction efficiency (expressed as %) was determined by counting the number of b-galactosidase positive cells in three high power fields per tumor nodule, divided by the total number of cells×100. A high level of transduction of cells (35.7±1.4%; Table 4) was observed throughout the tumor nodules in Mx-nBg vector-treated animals.

To further investigate the high transduction efficiency observed in the tumor nodules, a vector distribution study was conducted by intravenous injection of the Mx-nBg vector one hour and 24 hrs prior to sacrifice. Immunohistochemical staining for the retroviral envelope protein, using the 83A25 rat monoclonal antibody, showed that the accumulation of vector particles at 1 hr was pronounced in angiogenic areas interlaced throughout the tumor nodule, while no immunoreactivity for vector particles was observed at 24 hrs, indicating that viral entry into tumor and tumor-associated cells had occurred. Mason trichrome stain of the tumor nodules revealed that the angiogenic vascular beds were incompletely lined by endothelial cells, thus exposing extracellular matrix components to circulating blood elements. Conceivably, the exposure of collagen within the permeable tumor vasculature enhanced the local concentration of the matrix-targeted retroviral particles, which combined with the high mitotic index observed within the tumor nodule, facilitated the efficient transduction of tumor cells and associated vasculature. Mason trichrome stain confirmed that active fibrosis with abundant collagen deposition constituted a significant proportion of the residual nodule relative to the actual tumor mass.

Apoptosis is a known consequence of cyclin G1 blockade in both neoplastic cells (Skotzko et al., Cancer Res. 55, 5493–5498, 1995) and hyperplastic vascular cells (Zhu et al., Circulation 96, 628–635. 1997). Accordingly, immunohistochemical staining of the tumors treated with the Mx-dnG1 vector revealed a markedly increased incidence of TUNEL-positive apoptotic cells, when compared to those of control vector-treated animals. Apoptosis was not detected in angiogenic vessels of control vector-treated mice. In contrast, extensive apoptosis of endothelial cells (36±5%) in areas of angiogenesis was observed in the Mx-dnG1 vector-treated animals, as well as in the stromal compartment.

Notably, the increased incidence of apoptosis was not only restricted to the peripheral surfaces of the tumor nodules, but extended to many cell layers deep in the tumor nodules. The ability of the Mx-dnG1 vector to penetrate the tumor nodules was apparently facilitated by collagen deposition and/or exposure as well as vascular permeability within the core of the solid tumors. Consistent with this concept are the results of immunohistochemical studies which demonstrated that the accumulation of vector particles was most pronounced in angiogenic areas. Further, the destruction of proliferative endothelial cells and stromal cells observed, could by itself induce a disproportionate amount of tumor cell death by depletion of vascular supply (Folkman, Nature Med. 1, 27–3.1995; Hanahan & Folkman, Cell 86, 353–364. 1996; Fidler, J. Natl. Cancer Inst. 87,1588–1592. 1995) or growth factor stimuli (Fukumura et al., Cell 94, 715–725.1998).

Long term efficacy studies consisting of two (10-day) treatment cycles with the Mx-dnG1 vector (vector dose: $1 \times 10^7$ cfu), an equivalent dose of a non-targeted CAE-dnG1 vector, or an equal volume of PBS placebo, with an intervening rest period, confirmed that the therapeutic efficacy was dependent upon the collagen-targeting peptide motif incorporated into the primary structure of the amphotropic MLV envelope protein (FIGS. 14A & 14B). A rapid increase in tumor size was noted in the placebo-treated mice, while a marginal inhibition of tumor growth was observed in the non-targeted CAE-dnG1 vector-treated animals when compared to the PBS control (p=0.10; Table 3). In contrast, tumor growth was significantly inhibited in Mx-dnG1 vector-treated mice compared to the non-targeted CAE-dnG1 vector-treated-mice (p=0.014), the control targeted Mx-nBg vector-treated mice (p=0.004), and the PBS-treated mice (p=0.001; Table 3). Further, the tumor growth rate in Mx-dnG1 vector-treated mice remained consistently slower than that of the non-targeted CAE-dnG1 vector-treated animals (FIG. 14A) throughout the ~7-week follow-up period.

Kaplan-Meier survival studies were conducted in mice treated with PBS placebo, the non-targeted CAE-dnG1 vector or the matrix-targeted Mx-dnG1 vector (FIG. 14B). For ethical reasons, in lieu of actual animal mortality, the survival endpoint was established as the time to tumor quadrupling in lieu of actual subject mortality (recorded as the first time that the tumor burden was observed to be four times greater than initial baseline). If the tumor volume had not quadrupled by 47 days, the animal was sacrificed and the quadrupling time was censored at 47 days. The Kaplan-Meier product limit method (Kaplan & Meier J. Amer. Statist. Assoc. 53, 457, 1958) was used to estimate the probability of tumor quadrupling as a function of time (days). The Tarone test for trend (based on the logrank test; Tarone, Biometrika 62, 679, 1975) was used to compare the quadrupling times of the placebo (PBS)-treated, the non-targeted CAE-dnG1 vector-treated, and the matrix-targeted Mx-dnG1 vector-treated groups. Using the logrank test, the over-all p value for comparing all three groups simultaneously was 0.003, with a trend that was significant to a level of 0.004. These data indicate that the probability of long term control of tumor growth was significantly greater with the matrix-targeted Mx-dnG1 vector than with the non-targeted CAE-dnG1 vector or PBS placebo.

To evaluate the potential toxicity of the matrix-targeted vector, non-target organs were harvested at the end of one or two treatment cycles (cumulative vector dose: $8 \times 10^7$ or $1.6 \times 10^8$ cfu, respectively). Serum chemistry profiles were normal and histologic examination of bone marrow, lung, heart, brain, liver, kidney, testes, colon and skin revealed no evidence of organ damage. These results provide further support for the concept (Gordon et al., Cancer Res. 60, 3343–3347, 2000) that intravenous injection of the Mx-dnG1 retroviral vector appears to have a wide margin of safety.

TABLE 3

Inhibition of Tumor Growth In Vivo by Peripheral Vein Injection of Matrix-targeted Retroviral Vector Bearing a Cytocidal Cyclin G1 Construct

| Vector Name No. of Animals | Average Rate of Tumor Growth per Day (95% Confidence Interval) | p Value |
|---|---|---|
| Mx-dnG1 N = 10 | −6.1% (−9.5%, −2.5%) | |
| Mx-nBg N = 4 | 6.3% (−0.3%, 13.4%) | 0.004 |
| CAE-dnG1 N = 4 | 4.1% (−3.3%, 12.1%) | 0.014 |
| PBS (Placebo) N = 3 | 12.0% (2.8%, 21.9%) | 0.001 |

PBS vs. Mx-nBg: p = 0.37; PBS vs. CAE-dnG1: p = 0.10

Note:
The results of three separate experiments were combined. To compare the different vectors within each of the three experiments, a weighted analysis of variance was used with the estimated slopes as the dependent variable. For experiments I and II, the F-test based on the analysis of variance was used to compare the Mx-nBg and Mx-dnG1 vectors, and for experiment III, the F-test followed by least significant difference method of multiple comparisons was used to compare the Mx-dnG1 to the CAE-dnG1 vector and placebo treatments. The combined results of the analyzed data are shown above.

TABLE 4

Efficiency of Gene Delivery In Vivo by Peripheral Vein Injection of a Matrix-targeted Retroviral Vector

| Animal No. | Total Number of Cells Counted | Number of Transduced Tumor Cells | Transduction Efficiency, % Vector Dose: ~3 × 10⁶ cfu/gm |
|---|---|---|---|
| 1 | 2901 | 993 | 34.4 |
| 2 | 3002 | 1129 | 37.6 |
| 3 | 2359 | 811 | 34.3 |
| 4 | 3230 | 1175 | 36.3 |
| Mean ± S.D. | 2873 ± 319 | 1027 ± 142 | 35.7 ± 1.4 |

Note:
The efficiency of gene delivery into solid tumors by the Mx-nBg retroviral vector was evaluated in two subsets of animals after seven vector doses had been administered (see also FIG. 13). Transduction efficiency was determined by immunohistochemical staining of the tumor nodules, using a mouse monoclonal antibody directed against the b-galactosidase antigen followed by analysis using an Optimas imaging system. Transduction efficiency (expressed as %) was determined by counting the number of b-galactosidase positive cells in three high power fields per tumor nodule, divided by the total number of cells × 100.

Discussion

The results of example 3 demonstrate that the matrix-targeted retroviral vector, deployed by peripheral vein injection (i) accumulated in angiogenic tumor vasculature within one hour, (ii) transduced tumor cells with high level efficiency, and (iii) enhanced therapeutic gene delivery and long term efficacy without eliciting appreciable toxicity. Taken together, these results provide the first definitive proof of principle that a matrix-targeted retroviral vector directly injected into a peripheral vein improves therapeutic gene delivery into solid tumors.

The disclosures of all patents, publications (including published patent applications), database accession numbers, and depository accession numbers are herein incorporated by reference to the same extent as if each patent, publication, database accession number, and depository accessory number were specifically and individually incorporated by reference.

It is to be understood, however, that the scope of the present invention is not to be limited to the specific embodiments described above. The invention may be practiced other than as described particularly and still be within the scope of the accompanying claims.

What is claimed is:

1. A gene construct encoding a mutated human cyclin G1 protein wherein said mutated human cyclin G1 protein consists essentially of amino acid residues 41 to 249 of human cyclin G1 protein.

2. An expression vehicle comprising the gene construct of claim 1.

3. The expression vehicle of claim 2 wherein said expression vehicle is a viral vector.

4. The expression vehicle of claim 3 wherein said viral vector is a retroviral vector.

5. The expression vehicle of claim 3 wherein said viral vector is an adenoviral vector.

6. A gene construct encoding a mutated human cyclin G1 protein wherein said mutated human cyclin G1 protein consists essentially of human cyclin G1 protein wherein amino acid residue 61 of said human cyclin G1 protein has been changed to alanine.

7. An expression vehicle comprising the gene construct of claim 6.

8. The expression vehicle of claim 7 wherein said expression vehicle is a viral vector.

9. The expression vehicle of claim 8 wherein said viral vector is a retroviral vector.

10. The expression vehicle of claim 8 wherein said viral vector is an adenoviral vector.

* * * * *